(12) United States Patent
Zurawski, Jr. et al.

(10) Patent No.: US 9,034,303 B2
(45) Date of Patent: May 19, 2015

(54) NEUROPROTECTIVE AND NEURO-RESTORATIVE IRON CHELATORS AND MONOAMINE OXIDASE INHIBITORS AND USES THEREOF

(76) Inventors: Vincent R. Zurawski, Jr., Westtown, PA (US); David M. Stout, Chardon, OH (US); Theodore J. Nitz, Boyds, MD (US); Moussa B. H. Youdim, Nesher (IL); Orly Weinreb, Haifa (IL)

( * ) Notice: Subject to any disclaimer, the term of this patent is extended or adjusted under 35 U.S.C. 154(b) by 70 days.

(21) Appl. No.: 13/816,874

(22) PCT Filed: Aug. 12, 2011

(86) PCT No.: PCT/IB2011/053590
§ 371 (c)(1),
(2), (4) Date: Aug. 26, 2013

(87) PCT Pub. No.: WO2012/020389
PCT Pub. Date: Feb. 16, 2012

(65) Prior Publication Data
US 2013/0330284 A1 Dec. 12, 2013

Related U.S. Application Data

(60) Provisional application No. 61/373,403, filed on Aug. 13, 2010.

(51) Int. Cl.
C07D 215/28 (2006.01)
C07D 215/26 (2006.01)
C07D 215/32 (2006.01)
C07D 405/06 (2006.01)

(52) U.S. Cl.
CPC ............ *C07D 215/26* (2013.01); *C07D 215/28* (2013.01); *C07D 215/32* (2013.01); *C07D 405/06* (2013.01)

(58) Field of Classification Search
CPC ............................. C07D 215/28; C07D 215/32
USPC .......................................... 546/159; 514/312
See application file for complete search history.

(56) References Cited

U.S. PATENT DOCUMENTS

| 6,855,711 | B1 | 2/2005 | Youdim et al. |
| 2006/0234927 | A1 | 10/2006 | Youdim et al. |
| 2012/0040993 | A1 | 2/2012 | Youdim et al. |

FOREIGN PATENT DOCUMENTS

| WO | 2004/041151 | * | 5/2004 |
| WO | 2004/041151 | A2 | 5/2004 |
| WO | 2010/086860 | * | 8/2010 |
| WO | 2010/086860 | A3 | 2/2011 |

OTHER PUBLICATIONS

Qian, Optics communications, vol. 283, No. 10, May 2010, pp. 2228-2233.*
Gassen, M. et al, "Apomorphine is a highly potent free radical scavenger in rat brain mitochondrial fraction", European Journal of Pharmacology, pp. 219-225, vol. 308 No. 2 (Apr. 1996).
Yogev-Falach, M. et al, "The importance of propargylamine moiety in the anti-Parkinson drug rasagiline and its derivatives for MAPK-dependent amyloid precursor protein processing.", Federation of American Societies for Experimental Biology Journal, pp. 2325-2327, (Oct. 2003).
Tipton, K.F.et al, "Monoamine oxidases (MAO): Functions in the nervous system" Encyclopedia of Neuroscience,, Elsevier Science BV, Amsterdam, 3rd Edition (2004).
Qian et al, "Synthesis and third-order optical nonlinearities of nickel complexes of 8-hydroxyquinoline derivatives" Optics Communication, pp. 2228-2233, vol. 283, No. 10 (Jan. 2010).
Chemical catalog database citation, XP-002661860, (Oct. 2011).

* cited by examiner

*Primary Examiner* — D M Seaman
(74) *Attorney, Agent, or Firm* — Browdy and Neimark, PLLC

(57) ABSTRACT

8-Hydroxy-quinoline derivatives and 8-ethers, 8-esters, 8-carbonates, 8-acyloxymethyl, 8-phosphates, (phosphoryloxy)methyl, and 8-carbamates derivatives thereof are described that exhibit iron chelation, neuroprotective, neurorestorative, apoptotic and/or selective MAO-AB inhibitory activities.

19 Claims, 5 Drawing Sheets

NEUROPROTECTIVE AND NEURO-RESTORATIVE IRON CHELATORS AND MONOAMINE OXIDASE INHIBITORS AND USES THEREOF

FIELD OF THE INVENTION

The present invention relates to novel multifunctional neuroprotective compounds, in particular to quinoline derivatives possessing an iron chelator function and residues that impart antiapoptotic and neuroprotective functions, and brain MAO inhibition (preferably with little or no MAO inhibition in liver and small intestine).

BACKGROUND OF THE INVENTION

Iron is known to enhance the production of the highly reactive and toxic hydroxyl radical, thus stimulating oxidative damage. Iron has been associated with a number of diseases, disorders and conditions because humans have no physiologic means of eliminating excess iron. Examples of such diseases, disorders and conditions include hereditary hemochromatosis and thalassemias that were initially treated with deferoxamine (DFO), a naturally occurring siderophore, introduced in early 1960s, later substituted by the orally-active iron chelator, deferiprone (L1), and more recently by the orally-active drug deferasirox.

Neurodegenerative diseases, such as Parkinson's disease (PD) and Alzheimer's disease (AD), are neurodegenerative syndromes for which at present no cure is available. Both diseases are the most widespread neurodegenerative disorders and affect approximately 0.5% and 4-8%, respectively, of the population over the age of 50 years, forming an increasing economic burden for society.

Numerous studies including in vivo, in vitro and relevant animal models have shown a linkage between hydroxyl and oxygen free radicals production and neurodegenerative diseases and disorders, such as Parkinson's diseases, Alzheimer's disease and stroke as well as ALS, multiple sclerosis, Friedreich's ataxia, neurodegeneration with brain iron accumulation (NBIA) disease, epilepsy and neurotrauma. For this reason, 8-hydroxyquinolines and hydroxypyridinones have been proposed for iron binding as antioxidant-type drugs. Since iron accumulation in neurodegenerative diseases is a common feature, it has previously been shown that it has a pivotal role in the process of neurodegenration (Youdim, 1988) as well as age related macular degeneration (AMD) (Hahn P, Milam A H, Dunaief J L, 2003). Maculas affected by age-related macular degeneration contain increased chelatable iron in the retinal pigment epithelium. Gassen and Youdim (1999) and others, including Cuajungco et al. (2000) and Sayre et al. (2000), have suggested on several occasions the development of iron chelators as therapeutic agents for Alzheimer's disease and Parkinson's disease as well as for treatment of age related macular degeneration.

In Parkinson's disease, the brain defensive mechanisms against the formation of oxygen free radicals are defective. In the substantia nigra of Parkinsonian brains there are reductions in activities of antioxidant enzymes. Moreover, iron concentrations are significantly elevated in Parkinsonian substantia nigra pars compacta and within the melanized dopamine neurons. Recent studies have also shown that significant accumulations of iron in white matter tracts and neurons throughout the brain but especially in the substantia nigra pars compacta precede the onset of neurodegeneration and movement disorder symptoms. Indeed the accumulation of iron at the sites of neurodegeneration is one of the mysteries of neurodegenerative diseases because iron does not cross the blood-brain barrier (BBB).

The etiology of Alzheimer's disease (AD) and the mechanism of cholinergic neuron degeneration remain elusive. Nevertheless, the chemical pathology of AD shows many similarities to Parkinson's disease: the involvement of increased iron, release of cytochrome C, increased alpha-synuclein aggregation, oxidative stress, loss of tissue reduced glutathione (GSH, an essential factor for removal of hydrogen peroxide), reduction in mitochondrial complex I activity, increased lipid peroxidation, and loss of calcium-binding protein 28-kDa calbindin, to mention a few. These similarities also include the progressive nature of the disease, proliferation of reactive microglia around and on top of the dying neurons, the onset of oxidative stress, and inflammatory processes.

Oxygen free radicals have been shown to be associated with protein denaturation, enzyme inactivation, and DNA damage, resulting in lipid peroxidation of cell membranes, and finally cell death in neurodegenerative diseases. One of the profound aspects of neurodegenerative diseases is the accumulation and deposition of significant amounts of iron at the neurodegenerative sites. In AD, iron accumulates within the microglia and within the neurons and in plaques and tangles. Current reports have provided evidence that the pathogenesis of AD is linked to the characteristic neocortical beta-amyloid deposition, which may be mediated by abnormal interaction with metals such as iron. Indeed, iron is thought to cause aggregation of not only beta-amyloid protein but also of alpha-synuclein, promoting a greater neurotoxicity. This has led to the notion that chelatable free iron may have a pivotal role in the induction of the oxidative stress and the inflammatory process leading to apoptosis of neurons. Iron and radical oxygen species activate the proinflammatory transcription factor, NFκB, which is thought to be responsible for promotion of the cytotoxic proinflammatory cytokines IL-1, IL-6 and TNF-alpha, which increase in AD brains is one feature of AD pathology. This is considered logical since iron, as a transition metal, participates in Fenton chemistry with hydrogen peroxide to generate the most reactive of all radical oxygen species, reactive hydroxyl radical. This radical has been implicated in the pathology of cell death and mechanism of action of numerous toxins and neurotoxins (6-hydroxy-dopamine, MPTP, kainite, streptocozin model of AD). Furthermore, such toxins mimic many of the pathologies of neurodegenerative diseases (AD, Parkinson's disease and Huntington's Chorea), one feature of which is the accumulation of iron, but not of other metals, at the site of neurodegeneration.

Iron alone or iron decompartmentalized from its binding site by a neurotoxin, e.g. the dopaminergic neurotoxin 6-hydroxydopamine (6-OHDA), may induce oxidative stress and neurodegeneration, as evidenced in previous studies of the inventors in which intranigral administration of iron-induced "Parkinsonism" in rats and the iron chelator desferrioxamine protected the rats against 6-OHDA-induced lesions of nigrostrial dopamine neurons (Ben-Shachar et al., 1991). It has thus been suggested that treatment or retardation of the process of dopaminergic neurodegeneration in the substantia nigra may be affected by iron chelators capable of crossing the blood brain barrier in a fashion similar to the copper chelator D-penacillamine used in the treatment of Wilson's disease. This therapeutic approach for the treatment of Parkinson's disease can be applied to other metal-associated neurological disorders such as tardive dyskinesia, Alzheimer's disease and NBIA.

Stroke is the third leading cause of death in the Western world today, exceeded only by heart diseases and cancer. The overall prevalence of the disease is 0.5-0.8% of the population. Stroke is characterized by a sudden appearance of neurological disorders such as paralysis of limbs, speech and memory disorders, sight and hearing defects, etc., which result from a cerebrovascular damage.

Haemorrhage and ischemia are the two major causes of stroke. The impairment of normal blood supply to the brain is associated with a rapid damage to normal cell metabolism including impaired respiration and energy metabolism lact-acidosis, impaired cellular calcium homeostasis release of excitatory neurotransmitters, elevated oxidative stress, formation of free radicals, etc. Ultimately these events lead to cerebral cell death and neurological disfunction.

Treatment of stroke is primarily surgical. Much effort is being invested in less aggressive therapeutical intervention in the search for drugs which are capable of restoring normal blood perfusion in the damaged area as well as drugs which are designed to overcome the above listed damaging events associated with cellular damage.

Oxidative stress and free radical formation play a major role in tissue injury and cell death. These processes are catalyzed by transient metal ions, mainly iron and copper. In the case of stroke, since vascular damage is involved, iron is available for the free radical formation, a process that could be prevented by iron chelators. Indeed, with lazaroides (21-amino steroids), known free radical scavengers, a significant improvement of local and global ischemia damages induced in animals has been achieved.

Iron chelators and radical scavengers have been shown to have potent neuroprotective activity in animal models of neurodegeneration. However, the major problem with such compounds is that they do not cross the BBB. The prototype iron chelator Desferal (desferrioxamine) was first shown by M. Youdim to be a highly potent neuroprotective agent in animal models of Parkinson's disease (Ben-Schachar et al., 1991). However, Desferal does not cross the BBB and has to be injected centrally. Desferal also protects against streptozocin model of diabetes.

Free radicals in living organism are believed to be produced by the reaction of transition metal ions (especially copper and iron) with highly reactive species such as $H_2O_2$, $[O_2^-]$, thiols, and lipid peroxides. Antioxidant metal chelators, by binding free metal ions (especially copper and iron) or metal ions from active centers of enzymes of the defense system, can influence the oxidant/antioxidant balance in vivo, and hence, may affect the process of dopaminergic and cholinergic neurodegeneration and have great therapeutic potential against neuodegenerative diseases.

Iron accumulation in aging and the resulting oxidative stress has been suggested to be a potential causal factor in aging and age-related neurodegenerative disorders (Butterfield et al., 2001). There is increasing evidence that reactive oxygen species play a pivotal role in the process of ageing and the skin, as the outermost barrier of the body, is exposed to various exogenous sources of oxidative stress, in particular UV-irradiation. These are believed to be responsible for the extrinsic type of skin ageing, termed photo-ageing (Podda et al., 2001). Iron chelators have thus been suggested to favor successful ageing in general, and when applied topically, successful skin ageing (Polla et al., 2003).

Iron is a factor in skin photodamage, not only in ageing, apparently by way of its participation in oxygen radical production. Certain topical iron chelators are found to be photo-protective (Bisset and McBride, 1996; Kitazawa et al., 1999). UVA radiation-induced oxidative damage to lipids and proteins in skin fibroblasts was shown to be dependent on iron and singlet oxygen (Vile and Tyrrel, 1995). Iron chelators can thus be used in cosmetic and non-cosmetic formulations, optionally with sunscreen compositions, to provide protection against UV radiation exposure.

Other diseases, disorders or conditions associated with iron overload include: (i) viral infections, including HIV infection and AIDS where oxidative stress and iron have been described to be important in the activation of HIV-1 and iron chelation, and when, in combination with antivirals, might add to improve the treatment of viral, particularly HIV disease (van Asbeck et al., 2001); (ii) protozoal, e.g. malaria, infections; (iii) yeast, e.g. *Candida albicans*, infections; (iv) cancer where several iron chelators have been shown to exhibit anti-tumor activity and may be used for cancer therapy either alone or in combination with other anti-cancer therapies (Buss et al., 2003); (v) iron chelators may prevent cardiotoxicity induced by anthracycline neoplastic drugs (Hershko et al., 1996); (vi) inflammatotory disorders where iron and oxidative stress have been shown to be associated with inflammatory joint diseases such as rheumatoid arthritis (Andrews et al., 1987; Hewitt et al., 1989; Ostrakhovitch et al., 2001); (vii) diabetes where iron chelators have been shown to delay diabetes in diabetic model rats (Roza et al., 1994); (viii) iron chelators have been described to be potential candidates for treatment of cardiovascular diseases, e.g. to prevent the damage associated with free radical generation in reperfusion injury (Hershko, 1994; Flaherty et al., 1991); (ix) iron chelators may be useful ex-vivo for preservation of organs intended for transplantation such as heart, lung or kidney (Hershko, 1994).

One of the main problems in the use of chelating agents as antioxidant-type drugs is the limited transport of these ligands or their metal complexes through cell membranes or other biological barriers.

Drugs with the brain as the site of action should, in general, be able to cross the blood brain barrier (BBB) in order to attain maximal in vivo biological activity. The efficacy of the best established iron-chelating drug, Desferal, in the neurodegenerative diseases, is limited by its ineffective transport property and high cerebro- and oculotoxicity.

8-Hydroxyquinoline is a strong chelating agent for iron, and contains two aromatic rings, which can scavenge free radicals by themselves. In the U.S. Pat. No. 6,855,711, various iron chelators have been disclosed and their action in Parkinson's disease prevention has been shown. The lead compound, 5-[4-(2-hydroxyethyl)piperazin-1-ylmethyl]-8-hydroxyquinoline, was able to cross the BBB and was shown to be active against 6-hydroxydopamine (6-OHDA) in an animal model of Parkinson's disease.

PCT Publication. WO 2004/041151 discloses various iron chelators and multifunctional compounds shown to prevent Parkinson's disease. The lead compound M30 was able to cross the BBB and was shown to be active against 6-hydroxydopamine (6-OHDA) in an animal model of Parkinson's disease.

It would be very desirable to provide novel iron chelators that exhibit also neuroprotective activity, good transport properties through cell membranes including the blood brain barrier, optimal oral uptake and optimal or sufficient oral uptake and PK behavior that would qualify them as drug candidates for clinical development.

SUMMARY OF THE INVENTION

It has now been found by the present inventors that by modifying the 8-hydroxyquinolines disclosed in WO 2004/

041151, particularly the compound designated M30, in the ring and/or at positions 5 and 8, or both, multifunctional compounds derivatives can be obtained that have good transport properties in lipophilic media and are able to cross through cell membranes including the blood brain barrier, have optimal or sufficient oral uptake and pharmacokinetic (PK) behavior that qualify them as drug candidates for clinical development.

The present invention thus relates, in one aspect, to a compound of Formula I described hereinafter and pharmaceutically acceptable salts thereof. In one preferred embodiment, the compounds of the invention are those of Formula II herein.

The compounds of Formula I are multifunctional compounds comprising an iron chelator function and a residue that imparts both antiapoptotic and neuroprotective functions to the compound as well as brain MAO inhibition function (preferably with little or no MAO inhibition in liver and small intestine).

The iron chelator function is provided preferably by an 8-hydroxyquinoline residue or other radicals at the 8-position still capable of chelating iron specifically, and the combined antiapoptotic and neuroprotective functions is preferably provided by a propargyl group.

The compounds of the present invention are useful for treatment and/or prevention of diseases, disorders and conditions associated with iron overload and oxidative stress such as, but not limited to, neurodegenerative and cerebrovascular diseases and disorders, neoplastic diseases, hemochromatosis, thalassemia, cardiovascular diseases, diabetes, inflammatory disorders, anthracycline cardiotoxicity, viral, protozoal and yeast infections, for retarding ageing, and for prevention and/or treatment of skin ageing and/or skin damage associated with skin ageing and/or exposure to sunlight and/or UV light.

The diseases, conditions and disorders that can be treated with the compounds of the invention include, without limitation, Alzheimer's disease, Parkinson's disease, Huntington's disease, stroke, amyotrophic lateral sclerosis (ALS), multiple sclerosis, Friedreich's ataxia, neurodegeneration with brain Iron accumulation (NBIA), epilepsy, neurotrauma, age-related macular degeneration, glaucoma, hemochromatosis and thalassemia.

In a further aspect, the present invention provides a pharmaceutical composition comprising a pharmaceutically acceptable carrier and a multifunctional compound of the invention or a pharmaceutically acceptable salt thereof.

In yet another aspect, the present invention provides a cosmetic composition comprising a multifunctional compound of the invention.

BRIEF DESCRIPTION OF THE FIGURES

FIG. 5A-*percentage* viable HepG2; and FIG. 5B-*percentage* cell death HepG2.

FIG. 6A-*percentage* viable SHSY-5Y and FIG. 6B—percentage cell death SHSY-5Y.

DETAILED DESCRIPTION OF THE INVENTION

Figure 1:
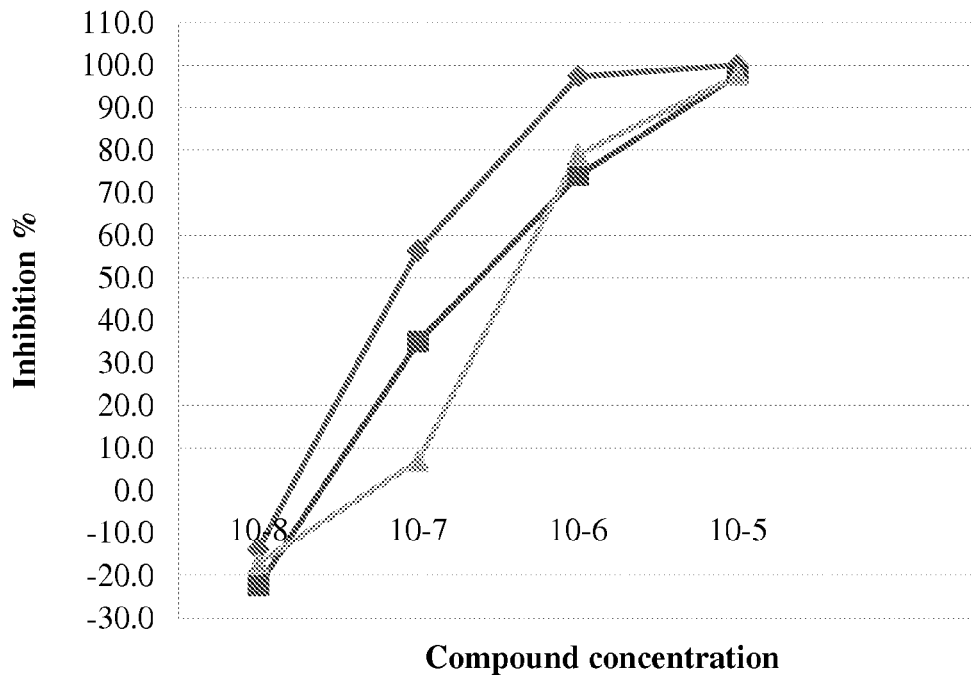
FIG. 1 shows inhibition of rat brain MAO-A by the compounds herein identified as compounds 3 (diamonds), 4 (squares) and M30 (triangles) in vitro.

The present invention provides compounds which are derivatives or analogs of the compound 5-[(methyl-2-propyn-1-ylamino)methyl]-8-quinolinol also known as 5-(N-propargyl-N-methylaminomethyl)-8-hydroxyquinoline (herein identified sometimes as M30) described in US 2006/0234927 and in WO 2004/041151, of the formula:

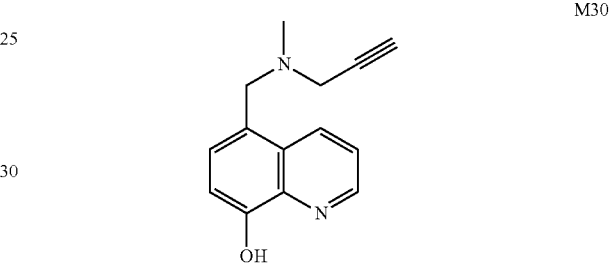

M30

Thus, in one aspect, the present invention relates to a compound of the formula I:

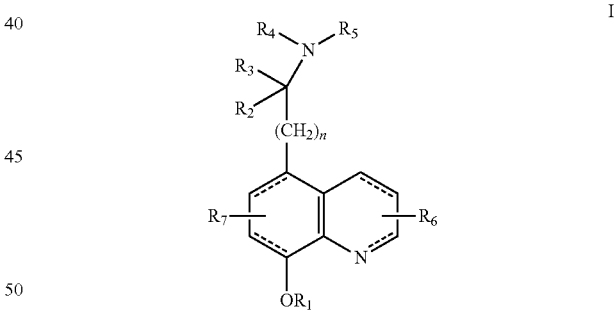

I wherein
$R_1$ is selected from:
  (i) H;
  (ii) $C_1$-$C_8$ alkyl substituted by one or more radicals selected from hydroxy, $C_1$-$C_8$ alkoxy, cyano, carboxy, aminocarbonyl, $C_1$-$C_8$ (alkyl)aminocarbonyl, di($C_1$-$C_8$)alkylaminocarbonyl, $C_1$-$C_8$ (alkoxy)carbonyl, or $C_1$-$C_8$ (alkyl)carbonyloxy;
  (iii) —$COR_8$, wherein $R_8$ is $C_1$-$C_8$ alkyl, $C_2$-$C_8$ alkenyl, $C_2$-$C_8$ alkynyl, $C_3$-$C_8$ cycloalkyl, aryl, heteroaryl, or heterocyclyl wherein said alkyl, alkenyl, alkynyl, aryl, heteroaryl, or heterocyclyl group is optionally substituted by one or more of the following groups: halogen atoms, $C_1$-$C_8$ alkyl, hydroxy, amino, $C_1$-$C_8$ alkylamino, di($C_1$-$C_8$)alkylamino, mercapto, $C_1$-$C_8$ alkylthio, cyano, $C_1$-$C_8$ alkoxy, carboxy, $C_1$-$C_8$ (alkoxy)carbonyl, $C_1$-$C_8$ (alkyl)carbonyloxy, $C_1$-$C_8$ (alkyl)sulfonyl, $C_1$-$C_8$ (alkyl)carbonylamino, aminocarbonyl, $C_1$-$C_8$ (alkyl)aminocarbonyl, or di($C_1$-$C_8$)alkylaminocarbonyl, or a $C_1$-$C_5$ alkyl group is substituted by an amino group at the α-position to the CO group and may be further substituted by a group selected from hydroxy, methylthio, mercapto, phenyl, hydroxyphenyl, indolyl, aminocarbonyl, carboxy, amino, guanidino, and imidazolyl;

(iv) —COOR$_9$, wherein R$_9$ is $C_1$-$C_8$ alkyl optionally substituted by halogen, $C_1$-$C_8$ alkoxy, phenyl optionally substituted by nitro, hydroxy, carboxy, or $C_3$-$C_6$ cycloalkyl; $C_2$-$C_4$ alkenyl; $C_2$-$C_4$ alkynyl; $C_5$-$C_7$ cycloalkyl; or phenyl optionally substituted by halogen, amino, nitro, $C_1$-$C_8$ alkyl, $C_1$-$C_8$ (alkoxy)carbonyl, or $C_1$-$C_8$ alkoxy;

(v) —CH$_2$—O—CO—R$_{10}$, or —CH(CH$_3$)—O—CO—R$_{10}$, wherein R$_{10}$ is $C_1$-$C_8$ alkyl optionally substituted by halogen, $C_1$-$C_8$ alkoxy; $C_2$-$C_4$ alkenyl optionally substituted by phenyl; $C_3$-$C_6$ cycloalkyl; phenyl optionally substituted by $C_1$-$C_8$ alkoxy; or heteroaryl selected from furyl, thienyl, isoxazolyl, or pyridyl optionally substituted by halogen or $C_1$-$C_8$ alkyl;

(vi) —PO(OR$_{11}$)$_2$, —CH$_2$—O—PO(OR$_{11}$)$_2$ or —CH(CH$_3$)—O—PO(OR$_{11}$)$_2$, wherein R$_{11}$ is independently selected from H, $C_1$-$C_8$ alkyl, or $C_1$-$C_8$ alkyl optionally substituted by hydroxy, $C_1$-$C_8$ alkoxy, or $C_1$-$C_8$ (alkyl)carbonyloxy; and (vii) —CONR$_{12}$R$_{13}$, wherein R$_{12}$ and R$_{13}$ are independently selected from H, $C_1$-$C_8$ alkyl, $C_2$-$C_8$ alkenyl, $C_2$-$C_8$ alkynyl, $C_3$-$C_8$ cycloalkyl, aryl, arylalkyl, heteroaryl, or heterocyclyl wherein said alkyl, alkenyl, alkynyl, aryl, heteroaryl, heteroarylalkyl, heterocyclyl or heterocyclylalkyl group is optionally substituted by one or more of the groups: halogen atoms, $C_1$-$C_8$ alkyl, hydroxy, amino, $C_1$-$C_8$ alkylamino, di($C_1$-$C_8$)alkylamino, mercapto, $C_1$-$C_8$ alkylthio, cyano, $C_1$-$C_8$ alkoxy, carboxy, $C_1$-$C_8$ (alkoxy)carbonyl, $C_1$-$C_8$ (alkyl)carbonyloxy, $C_1$-$C_8$ (alkyl)sulfonyl, $C_1$-$C_8$ (alkyl)carbonylamino, aminocarbonyl, $C_1$-$C_8$ (alkyl)aminocarbonyl, and di($C_1$-$C_8$)alkylaminocarbonyl, or a $C_1$-$C_5$ alkyl group is substituted by a carboxy group at the α-position to the OCON group and may be further substituted by a group selected from hydroxy, methylthio, mercapto, phenyl, hydroxyphenyl, indolyl, aminocarbonyl, carboxy, amino, guanidino, and imidazolyl, or R$_{12}$ and R$_{13}$ together with the N atom to which they are attached form a 5 to 7 membered saturated ring optionally further containing a heteroatom selected from O, S and N, optionally substituted at the ring by $C_1$-$C_8$ alkyl, hydroxy, oxo, carboxy, $C_1$-$C_8$ alkoxycarbonyl, $C_1$-$C_8$ aminocarbonyl, $C_1$-$C_8$ alkylaminocarbonyl, $C_1$-$C_8$ dialkylaminocarbonyl, or $C_1$-$C_8$ alkoxy;

R$_2$ and R$_3$ each independently is H, $C_1$-$C_8$ alkyl, halogen, or halo($C_1$-$C_8$)alkyl;

R$_4$ is H or $C_1$-$C_8$ alkyl, and R$_5$ is propargyl, allyl, cyclobutyl, or cyclopropyl;

R$_6$ is H, $C_1$-$C_8$ alkyl, $C_1$-$C_8$ alkoxy, $C_1$-$C_8$ alkylthio, hydroxy, mercapto, amino, $C_1$-$C_8$ alkylamino, di($C_1$-$C_8$) alkylamino or oxo, thioxo, imino, or $C_1$-$C_8$ alkylimino at the 2- or 4-position of the ring;

R$_7$ is H, halogen, $C_1$-$C_8$ alkyl, perhalo $C_1$-$C_8$ alkyl, $C_3$-$C_8$ cycloalkyl, $C_1$-$C_8$ alkoxy, $C_1$-$C_8$ alkylthio, hydroxy, mercapto, amino, $C_1$-$C_8$ alkylamino, di($C_1$-$C_8$)alkylamino, cyano, $C_1$-$C_8$ alkylsulfonyl, $C_1$-$C_8$ alkylcarbonylamino, $C_1$-$C_8$ alkylcarbonyl($C_1$-$C_8$)amino, or $C_1$-$C_8$ alkylsulfonyl($C_1$-$C_8$)amino;

each of the dotted lines indicates a single or double bond; and n is 0-8, and pharmaceutically acceptable salts thereof, but excluding the compounds wherein R$_1$, R$_2$, R$_3$, R$_6$, R$_7$ are H; n is 0; R$_4$ is H or CH$_3$, and R$_5$ is propargyl, or R$_1$, R$_2$, R$_3$, R$_4$, R$_6$, R$_7$ are H; n is 1, and R$_5$ is propargyl.

In certain embodiments, the compound of the invention is a compound of formula Ia of the structure:

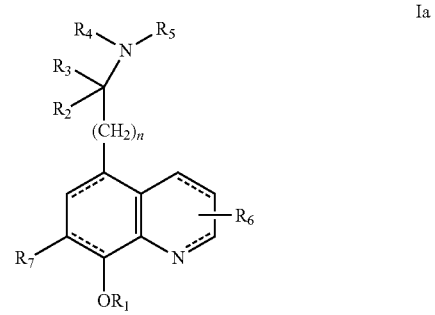

Ia wherein R$_1$ to R$_7$ are as defined above.

In certain preferred embodiments, the compound of the invention is a compound of the formula II:

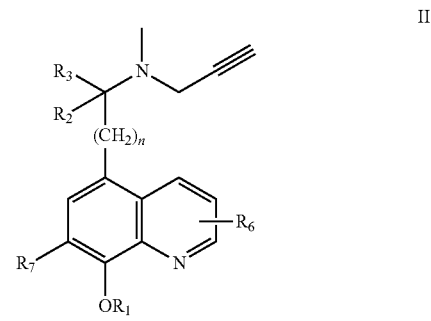

II wherein R$_1$, R$_2$, R$_3$ and R$_7$ are as defined above, R$_6$ is H and n is 0 to 2.

The term "halogen" as used herein refers to fluoro, chloro, bromo and iodo, and is preferably Cl or F. The radical may contain one or more halogen atoms and in certain embodiments it is CF$_3$.

The term "$C_1$-$C_8$ alkyl", alone or as part of a radical containing an alkyl group, typically means a straight or branched radical having 1 to 8, preferably 1 to 6, 5, 4, 3, 2 or 1 carbon atoms and includes, without being limited to, methyl, ethyl, n-propyl, isopropyl, n-butyl, sec-butyl, isobutyl, tert-butyl, n-pentyl, 1-methylbutyl, 2,2-dimethylpropyl, n-hexyl, n-heptyl, n-octyl, and the like. The alkyl radical may be substituted, without being limited to, by one or more OH, SH, COOH, CONH$_2$, CN, cycloalkyl (e.g., cyclohexyl, optionally substituted by alkyl), aryl (e.g., phenyl, optionally substituted by NO$_2$), alkoxy, alkoxycarbonyl, alkylcarbonyloxy, and heteroaryl or heterocyclyl (e.g., furyl, thienyl, piperidino). The term "halo($C_1$-$C_8$)alkyl" refers to $C_1$-$C_8$ alkyl, preferably $C_1$-$C_5$ alkyl substituted by one or more F atoms or by one or more F and Cl atoms. In certain embodiments the haloalkyl is pentafluoropentyl. In certain embodiments, the haloalkyl is methyl substituted by 1-3 F atoms or by F and Cl such as —CH$_2$F, —CHF$_2$, —CF$_3$, or —CClF$_2$.

The terms "$C_2$-$C_8$ alkenyl" and "$C_2$-$C_8$ alkynyl" typically mean a straight or branched radical having 2-8, preferably 2, 3 or 4, carbon atoms and one double or triple bond, respectively, and include, without being limited to, vinyl, allyl, prop-1-en-1-yl, prop-2-en-1-yl, but-3-en-1-yl, 2,2-dimethylvinyl, 2-ethenylbutyl, oct-3-en-1-yl, and the like, and ethynyl, propargyl, but-3-yn-1-yl, pent-3-yn-1-yl, and the like. The alkenyl radical may be substituted, for example, by aryl (e.g., phenyl).

The terms "$C_1$-$C_8$ alkoxy" and "$C_1$-$C_8$ alkylthio" as used herein typically mean a straight or branched radical having 1-8, preferably 1, 2, or 3 carbon atoms, and being preferably a substituent of an alkyl, phenyl or heteroaryl radical. Examples of alkoxy include methoxy, ethoxy, propoxy, isopropoxy, butoxy, pentoxy, and the like and of alkylthio include methylthio, ethylthio, propylthio, isopropylthio, butylthio and the like.

The term "$C_3$-$C_8$ cycloalkyl" refers herein to a mono- or bi-cyclic saturated hydrocarbyl group such as cyclopropyl, cyclobutyl, cyclopentyl, cyclohexyl, cycloheptyl, cyclooctyl, adamantyl, bicyclo[3.2.1]octyl, bicyclo[2.2.1] heptyl, and the like, that may be substituted, for example, by one or more alkyl groups.

The term "aryl" refers to a $C_6$-$C_{14}$ aryl, namely, to an aromatic carbocyclic group having 6 to 14 carbon atoms consisting of a single ring or multiple rings either condensed or linked by a covalent bond such as, but not limited to, phenyl, naphthyl, carbazolyl, phenanthryl, and biphenyl. In some preferred embodiments, the aryl radical is phenyl, optionally substituted by halogen (e.g., F), alkyl (e.g., methyl), alkoxy (e.g., methoxy), and nitro.

The term "heteroaryl" refers to a radical derived from a mono- or poly-cyclic heteroaromatic ring containing one to three heteroatoms selected from the group consisting of N, O and S. When the heteroaryl is a monocyclic ring, it is preferably a radical of a 5-6-membered ring such as, but not limited to, pyrrolyl, furyl, thienyl, pyrazolyl, imidazolyl, oxazolyl, isoxazolyl, thiazolyl, isothiazolyl, pyridyl, pyrimidinyl, 1,3,4-triazinyl, 1,2,3-triazinyl, and 1,3,4-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl and benzoxazolyl. It is to be understood that when a polycyclic heteroaromatic ring is substituted, the substitutions may be in any of the carbocyclic and/or heterocyclic rings. In some embodiments, the heteroaryl is furyl, thienyl, isoxazolyl, pyridyl (optionally substituted by Cl), indolyl, or imidazolyl.

The term "heterocyclyl" refers to a radical derived from a mono- or poly-cyclic non-aromatic ring containing one to three heteroatoms selected from the group consisting of N, O and S. Examples of such radicals include, without limitation, piperidinyl, 4-morpholinyl, or pyrrolidinyl.

As used herein, "n" is from 0 to 8, preferably from 0 to 5. In certain embodiments, n is 1 or 2.

In certain embodiments, the compounds of the invention of formula I and II above are derivatives or analogs of 5-[(methyl-2-propyn-1-ylamino)methyl]-8-quinolinol (M30) in which the 8-hydroxy group of the quinoline ring is modified in such a way that it still maintains its iron chelating function.

In certain embodiments, the derivatives are 8-ethers of M30, wherein $R_1$ is as defined above in (ii) and is preferably $C_1$-$C_3$ alkyl substituted by hydroxy or $C_1$-$C_3$ alkoxy, more preferably $R_1$ is hydroxypropyl, methoxypropyl or propoxymethyl. In certain embodiments, when $R_1$ is —$COR_8$ and $R_8$ is a $C_1$-$C_5$ alkyl group substituted by an amino group at the α-position to the CO group and optionally further substituted by a group selected from hydroxy, methylthio, mercapto, phenyl, 4-hydroxyphenyl, indolyl, aminocarbonyl, carboxy, amino, guanidino, and imidazolyl. The residue of proline is formed when $R_8$ is defined as heterocyclyl consisting of 2-pyrrolidinyl.

In certain embodiments, the derivatives are 8-esters of M30, wherein $R_1$ is —$COR_8$ as defined above in (iii). In certain embodiments, $R_8$ is $C_1$-$C_5$ alkyl, for example, methyl optionally substituted by methoxy, methoxycarbonyl, carboxy, methylcarbonyloxy or one or more of Cl or F atoms, e.g. methoxymethyl, methoxycarbonylmethyl, methylcarbonyloxymethyl, chloromethyl or trifluoromethyl, or ethyl optionally substituted by ethoxy, isobutyl, or sec-pentyl. In certain embodiments, $R_8$ is $C_2$-$C_4$ alkenyl, preferably vinyl optionally substituted by phenyl (e.g. 2-phenylvinyl), 1-methylvinyl, 2-methylvinyl, 2,2-dimethylvinyl, or but-3-en-1-yl. In certain embodiments, $R_8$ is $C_3$-$C_5$ cycloalkyl such as cyclopropyl or cyclopentyl; aryl such as phenyl optionally substituted by methoxy; preferably at position 4; heteroaryl such as 2-thienyl, 2-furyl, 5-isoxazolyl or pyridyl optionally substituted by Cl; or heterocyclyl such as 4-morpholinyl.

In certain embodiments, the derivatives are 8-carbonates of M30, wherein $R_1$ is —$COOR_9$ as defined above in (iv). In certain embodiments, $R_9$ is $C_1$-$C_8$ alkyl such as methyl optionally substituted by Cl, 4-nitrophenyl or $C_6$ cycloalkyl, ethyl optionally substituted by methoxy, e.g. 2-methoxyethyl, or one or more Cl or F atoms, e.g. 1-chloroethyl, 2-chloroethyl, 2-fluoroethyl, 2,2,2-trichloroethyl, or 2,2,2-trifluoroethyl, propyl, butyl, isobutyl, pentyl, or octyl; $C_2$-$C_3$ alkenyl such as vinyl, 1-methylvinyl or allyl; $C_3$-$C_4$ alkynyl such as propargyl or but-3-yn-yl; $C_5$-$C_6$ cycloalkyl such as cyclopentyl or cyclohexyl; or phenyl optionally substituted by nitro, fluoro, methoxy or methyl such as 4-nitrophenyl, 4-fluorophenyl, 4-methoxyphenyl, or 4-methylphenyl.

In certain embodiments, the derivatives are 8-acyloxymethyl derivatives of M30, wherein $R_1$ is —$CH_2$—O—CO—$R_{10}$, or —CH($CH_3$)—O—CO—$R_{10}$ as defined above in (v). In certain embodiments, $R_{10}$ is $C_1$-$C_5$ alkyl such as methyl optionally substituted by methoxy, methoxycarbonyl, methylcarbonyloxy, or one or more Cl or F atoms, e.g. chloromethyl of trifluoromethyl, ethyl optionally substituted by ethoxy, isobutyl, or 1-methylbutyl; $C_2$-$C_4$ alkenyl such as vinyl optionally substituted by phenyl, e.g. 2-phenylvinyl, 1-methylvinyl, 2-methylvinyl, 3-buten-1-yl, or 2,2-dimethylvinyl; $C_3$-$C_5$ cycloalkyl such as cyclopropyl or cyclopentyl; phenyl optionally substituted by methoxy such as 4-methoxyphenyl; or heteroaryl such as 2-furyl, 2-thienyl, 5-isoxazolyl, or pyridyl optionally substituted by halogen such as 2-chloro-pyrid-5-yl.

In certain embodiments, the derivatives are 8-phosphates or (phosphoryloxy)methyl derivatives of M30, wherein $R_1$ is —PO(O$R_{11}$)$_2$, —$CH_2$—O—PO(O$R_{11}$)$_2$ or —CH($CH_3$)—O—PO(O$R_{11}$)$_2$, as defined in (vi) above.

In certain embodiments, the derivatives are 8-carbamate derivatives of M30, wherein $R_1$ is —CON$R_{12}R_{13}$ as defined in (vii) above. When $R_{12}$ or $R_{13}$ is a $C_1$-$C_5$ alkyl group substituted by a carboxy group at the α-position to the —CON— group and optionally further substituted by a group selected from hydroxy, methylthio, mercapto, phenyl, 4-hydroxyphenyl, indolyl, aminocarbonyl, carboxy, amino, guanidino, and imidazolyl, the radical formed is a residue of a natural amino acid that typically occurs in proteins, including glycine, alanine, valine, leucine, isoleucine, lysine, valine, phenylalanine, glutamic acid, aspartic acid, asparagine, glutamine, arginine, histidine, proline, serine, tyrosine, methionine, threonine, and tryptophan. The residue of proline is formed when one of $R_{12}$ or $R_{13}$ is defined as heterocyclyl consisting of 2-pyrrolidinyl.

In certain embodiments, the compound of the invention is a derivative or analog of M30 modified at the quinoline ring. In certain embodiments, one or both of the carbocyclic ring or the heterocyclic ring of the quinoline structure may be hydrogenated, as indicated by the dotted lines in Formula I above. Examples of such compounds include the compounds in which $R_1$, $R_2$, $R_3$, $R_6$ and $R_7$ are H; $R_4$ is $CH_3$, $R_5$ is propargyl, n is 0, and the two dotted lines in the heterocylic ring or in the carbocyclic ring, respectively, represent single bonds. In certain embodiments, the quinoline ring may be substituted at either of the rings, for example, at the 7 position by a group $R_7$ which can be halogen, preferably F; $C_1$-$C_8$, preferably $C_1$-$C_3$ alkyl, more preferably, methyl, ethyl and isopropyl; or $C_3$-$C_8$ cycloalkyl, preferably cyclopropyl; or at any of the 2, 3 or 4 positions by $R_6$ which may be $C_1$-$C_8$ alkyl, $C_1$-$C_8$ alkoxy, $C_1$-$C_8$ alkylthio, hydroxy, mercapto, amino, $C_1$-$C_8$ alkylamino, or di($C_1$-$C_8$)alkylamino, and when the heterocyclic ring is partially hydrogenate, $R_6$ may also be oxo, thioxo, imino, or $C_1$-$C_8$ alkylimino Examples of compounds of formula II substituted at the 7-position include the compounds herein identified as compounds 1 and 2, in which $R_1$, $R_2$, $R_3$ and $R_6$ are H, n is 0, and $R_7$ is $CH_3$ or F, respectively.

In certain embodiments, the derivatives or analogs of M30 are substituted at the methylene group at the 5-position, namely, $R_2$ and/or $R_3$ may be $C_1$-$C_8$, preferably $C_1$-$C_3$ alkyl, more preferably methyl; halogen, preferably F; or —$CF_3$. Examples of such compounds include the compounds of formula II wherein $R_1$, $R_2$, $R_6$ and $R_7$ are H, n is 0, and $R_3$ is $CH_3$ or $CF_3$, and compound wherein $R_1$, $R_6$ and $R_7$ are H, and $R_2$ and $R_3$ each is F. In certain embodiments, the derivatives or analogs of M30 the methylene radical at the 5-position is replaced by a dimethylene or trimethylene radical, namely, n is 1 or 2. Examples of such compounds include: (i) the compounds of formula II, herein identified as compounds 3, 7 and 8, wherein n is 1, $R_1$, $R_2$, $R_3$, and $R_6$ are H, and $R_7$ is H, cyclopropyl, or F, respectively; (ii) the compound [O-Methyl-Compound 3], wherein $R_1$ is —$CH_3$, and each of $R_2$, $R_3$, $R_6$ and $R_7$ is H; and (iii) the compound of formula II, herein identified as compound 4, wherein n is 2, $R_1$, $R_2$, $R_3$, $R_6$ and $R_7$ are H.

The present invention further relates to pharmaceutically acceptable salts of the compounds including salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, formate, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, ethanesulfonate, 2-hydroxyethanesulfonate, and the like. Also contemplated are salts of amino acids such as arginate and the like and gluconate or galacturonate (see, for example, *Handbook of Pharmaceutical Salts, Properties, Selection, and Use*, Stahl, P. H. and Wermuth, C. G., Eds; VHCA and Wiley-VCH: Zurich and Weinheim, 2002).

The present invention further relates to the compound of the formula III, the 8-methyl ether of M30, herein referred to as O-Methyl-M30. Although not a strong iron chelator, this compound is shown in the examples hereinafter to exhibit interesting biological activities as MAO-A and MAO-B inhibitor:

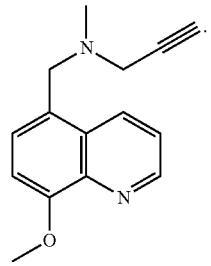

III

The compounds of the invention of Formula I are specific iron chelators that are suitable to bind unbound iron within the cells. Iron that is not bound to transferrin is the toxic form of iron. The iron chelators of the invention have good transport properties and cross cell membranes thus chelating the unbound iron in excess within the cells. It is expected that their complexes with iron will leave the cells freely and will be rapidly excreted. It is further expected that the compounds, or at least a major part of the compounds, will be able to cross the BBB and thus will be suitable candidates for treatment of neurodegenerative diseases, disorders and conditions.

In another aspect, the present invention relates to pharmaceutical compositions comprising a compound of the invention or a pharmaceutically acceptable salt thereof, in combination with a pharmaceutically acceptable carrier.

The compounds of the invention are useful for preventing and/or treating conditions, disorders or diseases that can be prevented and/or treated by iron chelation therapy and/or neuroprotection and neurorestoration, apoptotic activity, and/or selective MAO-AB inhibition.

In certain embodiments, the compounds are for use in the prevention and/or treatment of neurodegenerative and cerebrovascular diseases, conditions and disorders such as Parkinson's disease, Alzheimer's disease, stroke, amyotrophic lateral sclerosis (ALS), multiple sclerosis, Friedreich's ataxia, NBIA, epilepsy, and neurotrauma. The compounds can also be useful for promoting nerve regeneration, nerve restoration or to prevent or inhibit secondary degeneration which may otherwise follow primary nervous system injury, e.g., closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision.

In certain embodiments, the compounds of the invention are for use in the treatment of Parkinson's disease. In certain embodiments, the compounds are for treatment of Alzheimer's disease. In certain embodiments, the pharmaceutical composition is for treatment of a cerebrovascular disorder, particularly stroke. The "prevention" aspect of the use of the iron chelators of the invention in diseases such as Parkinson's disease and Alzheimer's disease involves the prevention of further neurodegeneration and of the further progress of the disease.

In certain embodiments, the compounds of the invention can be used for prevention and/or treatment of the following diseases or disorders: age related macular degeneration; glaucoma; diabetes; iron overload in hemochromatosis and thalassemia; cardiovascular diseases, e.g. to prevent the damage associated with free radical generation in reperfusion injury; inflammatory disorders such as a joint inflammatory disorder, particularly rheumatoid arthritis, inflammatory bowel disease (IBD), and psoriasis; anthracycline cardiotoxicity, in case of cancer patients being treated with anthracycline neoplastic drugs; protozoal infection such as malaria caused by *Plasmodium falciparum*; yeast infection such as *Candida albicans* infection; viral infection such as retroviral infection, e.g., HIV-1, for the treatment of AIDS, optionally in combination with one or more antiviral agents such as abacavir, atazanavir, combivir, darunavir, fosamprenavir, indinavir, lopinavir, nelfinavir, raltegravir, ritonavir, saquinavir, tenofovir, tipranavir, trizivir, or zidovudine.

In certain embodiments, the compounds can be used for retarding ageing and/or improving the ageing process by prevention of ageing-related diseases, disorders or conditions such as neurodegenerative diseases, disorders or conditions; and for prevention and/or treatment of skin ageing and/or skin damage associated with ageing and/or exposure to sunlight and/or UV light.

In certain embodiments, the present invention provides a cosmetic composition and a cosmeticeutically acceptable carrier, useful for topical application for prevention and/or treatment of skin ageing and/or skin damage associated with ageing and/or exposure to sunlight and/or UV light. The cosmetic composition may be in the form of a lotion or cream and may be administered with other agents for skin treatment.

In certain embodiments, the iron chelators are for use ex-vivo for preservation of organs intended for transplantation such as heart, lung or kidney.

In still another aspect, the present invention provides a method for iron chelation therapy which comprises administering to an individual in need thereof an effective amount of a compound of the invention or of a pharmaceutically acceptable salt thereof.

In certain embodiments, the present invention provides a method for the prevention and/treatment of a neurodegenerative disease, condition or disorder, which comprises administering to an individual in need thereof an effective amount of a compound of the invention or of a pharmaceutically acceptable salt thereof.

In certain embodiments, the present invention provides a method for the treatment of cancer, which comprises administering to an individual in need thereof an effective amount of a compound of the invention or of a pharmaceutically acceptable salt thereof. In certain embodiments, the iron chelator of the invention is administered before, concurrently or after administration of one or more chemotherapeutic agents.

In certain embodiments, the present invention provides a method for the prevention and/or treatment of iron overload in hemochromatosis or thalassemia patients, which comprises administering to said patient an effective amount of a compound of the invention or of a pharmaceutically acceptable salt thereof.

In certain embodiments, the present invention provides a method for prevention and/or treatment of cardiovascular diseases, e.g. to prevent the damage associated with free radical generation in reperfusion injury, which comprises administering to an individual in need thereof an effective amount of a compound of the invention or of a pharmaceutically acceptable salt thereof.

In certain embodiments, the present invention provides a method for prevention and/or treatment of diabetes, which comprises administering to an individual in need thereof an effective amount of a compound of the invention or of a pharmaceutically acceptable salt thereof.

In certain embodiments, the present invention provides a method for prevention and/or treatment of inflammatory disorders, which comprises administering to an individual in need thereof an effective amount of a compound of the invention or of a pharmaceutically acceptable salt thereof. In one preferred embodiment, the inflammatory disorder is a joint inflammatory disorder, particularly rheumatoid arthritis. In another preferred embodiment, the inflammatory disorder is inflammatory bowel disease (IBD). In a further preferred embodiment, the inflammatory disorder is psoriasis.

In certain embodiments, the present invention provides a method for prevention and/or treatment of anthracycline cardiotoxicity, which comprises administering to an individual undergoing treatment with anthracycline neoplastic drugs an effective amount of a compound of the invention or of a pharmaceutically acceptable salt thereof.

In certain embodiments, the present invention provides a method for prevention and/or treatment of a viral, protozoal or yeast infection which comprises administering to an individual in need thereof an effective amount of a compound of the invention or of a pharmaceutically acceptable salt thereof, alone or in combination with an antiviral, antiprotozoan or antifungal drug. In certain embodiments, the viral infection is a retroviral infection, e.g. HIV-1, and the compound is used in the treatment of AIDS, optionally in combination with antiviral agents. In certain embodiments, the protozoal infection is malaria caused by *Plasmodium falciparum*. In certain embodiments, the yeast infection is a *Candida albicans* infection.

In certain embodiments, the present invention provides a method for retarding ageing and/or improving the ageing process by prevention of ageing-related diseases, disorders or conditions which comprises administering to an individual in need thereof an effective amount of a compound of the invention or of a pharmaceutically acceptable salt thereof. The individual in need may be a healthy individual or an individual suffering from an age-related disease such as a neurodegenerative disease, disorder or condition.

In certain embodiments, the present invention provides a method for prevention and/or treatment of skin ageing and/or skin damage associated with ageing and/or exposure to sunlight and/or UV light, which comprises administering to an individual in need thereof an effective amount of a compound of the invention or of a pharmaceutically acceptable salt thereof. The compound is most preferably administered topically in a pharmaceutical or cosmetic formulation.

For preparing the pharmaceutical compositions of the present invention, methods well-known in the art can be used. Inert pharmaceutically acceptable carriers can be used that are either solid of liquid. Solid form preparations include powders, tablets, dispersible granules, capsules, cachets and suppositories.

A solid carrier can be one or more substances which may also act as diluents, flavoring agents, solubilizers, lubricants, suspending agents, binders, or tablet disintegrating agents; it can also be an encapsulating material.

Liquid pharmaceutical compositions include solutions, suspensions, and emulsions. As an example, water or water-propylene glycol solutions for parenteral injection may be mentioned. Liquid preparations can also be formulated in solution in aqueous poly(ethylene glycol) solution. Aqueous solutions for oral use can be prepared by dissolving the active component or pharmaceutically acceptable salts thereof in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical composition is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vial or ampoules. The unit dosage form can also be a capsule, cachet, or table itself or it can be the appropriate number of any of these packaged forms.

In therapeutic use for the treatment of Parkinson's disease, the compounds utilized in the pharmaceutical method of this invention may be administered to the patient at dosage levels of from 1 mg/kg to 20 mg/kg per day.

In therapeutic use for the treatment of stroke one or more dosages of from about 100 mg/kg to about 500 mg/kg of body weight may be administered to the patient as soon as possible after the event.

The dosage, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are intended as an illustration, and not as a limitation, of the scope of the invention.

According to the present invention, the new derivatives and analogs of M30 are synthesized and tested in succession for: (1) oral availability, (2) PK behavior, and (3) ability to penetrate the BBB and be taken up by brain tissue following administration. Derivatives meeting minimum levels of performance in these categories are tested for retention of the four characteristics cited above (1) iron chelation, (2) selective MAO-A/B inhibition, (3) antiapoptotic activity, and (4) neuro-rescue.

A simple starting approach leading to the least alteration in structure, thereby preserving as many desirably properties of the parent compound consists in modifying the compounds at the phenolic 8-hydroxyl group. One strategy for assessing the suitability of a prodrug to enhance the bioavailability and PK of each of the compounds is preparation of simple esters that gauge steric bulk as a factor in esterase hydrolysis. A resultant prodrug ester derivative is expected to provide for both better absorption and longer circulating $t_{1/2}$, depending upon the kinetics of plasma de-esterification known to be catalyzed by plasma esterases. In addition, esterification with amino acids may aid by amino acid active transport across the gut and the blood brain barrier. L-Valine is known to improve bioavailability of several drugs. Another strategy is etherification of the 8-hydroxyl group thus providing ether derivatives pro-drugs with a long-term stability in aqueous environment. A further strategy is to prepare carbonates that more readily expose the alcohol-leaving group to esterases and upon hydrolysis would spontaneously generate $CO_2$. The calculated Log P values of the compounds provide an array of values that are close to the ideal range of 2.5-3.5 and are typically higher than the value of 2.18 for M30.

In certain embodiments, the compounds of the invention are the compounds herein described in the Examples. These compounds are modified and are expected to have improved transport properties through cell membranes including the blood brain barrier and/or optimal or sufficient oral uptake and/or optimal or sufficient PK behavior that qualify them as drug candidates for clinical development and include a residue imparting combined antiapoptotic and neuroprotective functions that is a propargyl moiety.

As mentioned before, drugs with the brain as the site of action should, in general, be able to cross the blood brain barrier (BBB) in order to attain maximal in vivo biological activity. When the intention is to bring to the brain iron chelators to bind and remove iron that accumulates in the brain in some neurodegenerative diseases, one of the possible solutions is to design iron-chelating molecules with specific groups, responsible for amphiphilic behavior. Such amphiphilic groups possess lipophilic and hydrophilic centers. The size and structure of both centers control the overall lipophilicity of the whole molecule, and hence its transport properties.

EXAMPLES

The following examples describe the structure of compounds of the invention (Chemical Section) and their biological activity (Biological Section). These examples are intended as an illustration, and not as a limitation, of the scope of the invention.

I. Chemical Section

Example 1

Synthesis of 5-[(methyl-2-propyn-1-ylamino)methyl]-8-quinolinol (M30)

The synthesis of M30 is described herein below:

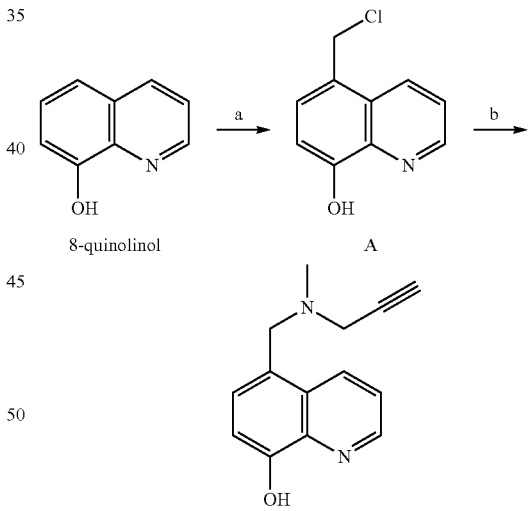

Reagents: (a) HCl (32%), HCHO (37%), 0 → rt; (b) N-methylpropargylamine, (Me₂CH)₂NEt, CHCl₃, rt.

A mixture of 14.6 g (0.1 mol) of 8-quinolinol, 16 mL of 32% HCl in water, and 16 mL (0.1 mL) of 37% formaldehyde in water at 0° C. was treated with hydrogen chloride gas for 6 h. The solution was allowed to stand at room temperature for 2 h without stirring. The yellow solid obtained was collected on a filter, washed with 90% alcohol and dried under vacuum to give 5-chloromethyl-8-quinolinol hydrochloride A (19.0 g, 98%): $^1$H NMR (250 MHz, CDCl$_3$, δ) 5.32 (s, 2H), 7.53 (m, 1H), 7.85 (m, 2H), 8.12 (m, 1H), 9.12 (m, 1H), 9.28 (m, 1H).

To a mixture of 5-chloromethyl-8-quinolinol hydrochloride A (2.707 g, 11.8 mmol) and diisopropylethylamine (DIPEA; 2.1 mL, 20.4 mmol, 2 eq) in 50 mL $CHCl_3$ at 0° C. was added N-methyl-N-propargylamine (10.2 mmol, 1 eq). The mixture was stirred for 24 h at room temperature. $CHCl_3$ (100 mL) was added and the solution obtained was washed with 5% $NaHCO_3$ (3×50 mL), brine (2×50 mL), and then dried over $Na_2SO_4$. The solution was filtered and evaporated to dryness. The residue was crystallized from a mixture of benzene-hexane (1:1) to yield M30 (80% yield): mp 232-233° C. (hydrochloric salt); $^1H$ NMR (250 MHz, $CDCl_3$, δ) 2.30 (dd, J=2.15, 2.14 Hz, 1H), 2.33 (s, 3H), 3.27 (d, J=2.20 Hz, 2H), 3.86 (s, 2H), 7.06 (d, J=7.72 Hz, 1H), 7.31 (m, 1H), 7.37 (d, J=7.73 Hz, 1H), 7.46 (dd, J=8.52 4.2 Hz, 1H), 8.60 (dd, J=8.52, 1.47 Hz, 1H), 8.76 (dd, J=4.01, 1.50 Hz, 1H); $^{13}C$ NMR (100 MHz, hydrochloric salt in $D_2O$, δ) 42.46, 47.54, 56.35, 74.18, 83.77, 118.22, 119.17, 125.83, 131.63, 132.06, 138.96, 145.46, 145.97, 152.20; Mass spectrometry: calculated for $C_{14}H_{14}N_2O$ m/z $[M+Na]^+$=249.27, found $[M+Na]^+$=249.23.

Example 2

Syntheses of esters of M30

The syntheses of esters of M30 are described herein below:

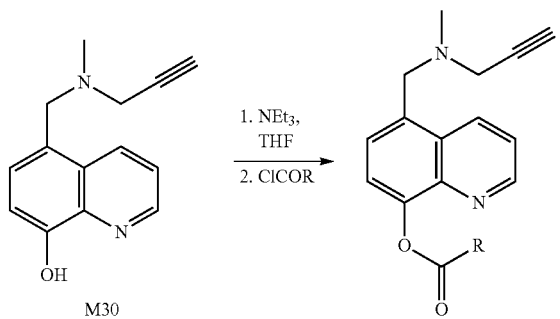

A solution of 1 eq M30 and 1.1 eq triethylamine (TEA) in tetrahydrofuran (THF) is treated by dropwise addition under a nitrogen atmosphere with a solution of 1 eq of the corresponding acid chloride (e.g., for R=—$CH_3$, acetyl chloride) in THF. After completion (TLC or HPLC analysis), the mixture is concentrated in vacuo and the residue is partitioned between ethyl acetate and water. The organic phase is dried with magnesium sulfate and evaporated in vacuo. The crude product is purified by crystallization or by column chromatography.

In this way the following esters can be prepared, having at the 8-position the groups: —$OCOCH_3$, —$OCOCH_2CH_3$, —$OCOCH(CH_3)CH_2CH_2CH_3$, —$OCOCH_2CH(CH_3)_2$, —$OCOCH_2Cl$, —$OCOCH_2OCH_3$, —$OCOCH_2CH_2OCH_2CH_3$, —$OCOCH=CH_2$, —$OCOC(CH_3)=CH_2$, —$OCOCH=CH(CH_3)$, —$OCOCH=CHPh$, —$OCOCH_2CH_2CH=CH_2$, —$OCOCH=C(CH_3)_2$, —$OCOCF_3$, —$OCOCH_2CO_2CH_3$, —$OCOCH_2O_2CCH_3$, —OCO(4-methoxyphenyl), —OCO(2-thienyl), —OCO(2-furyl), —OCOcyclopropyl, —OCOcyclopentyl, —OCO(5-methylisoxazolyl), —OCO(2-chloropyrid-5-yl), and —OCO(4-morpholinyl).

Example 3

Syntheses of Amino Acid Esters of M30

The syntheses of amino acid esters of M30 are described herein below:

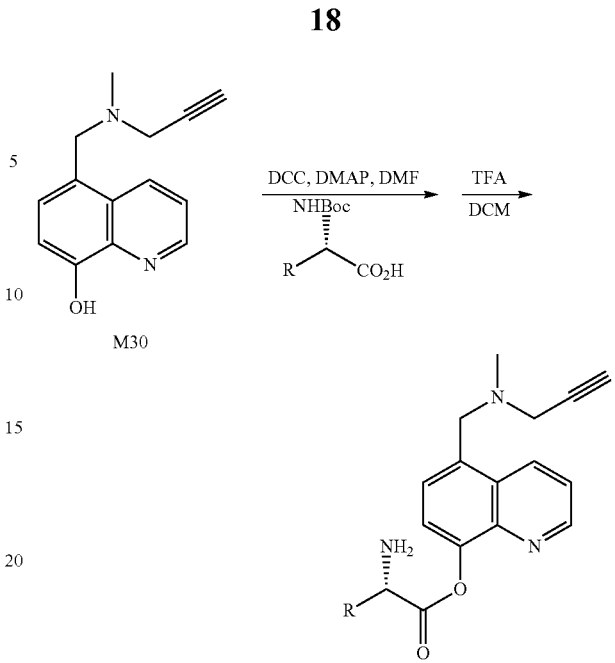

Using the procedure of Song, et al. (*J. Med. Chem.*, 2005, 48, 1274-1277), t-butoxycarbonyl (Boc) protected amino acids (5 eq), N,N'-dicyclohexylcarbodiimide (DCC; 5 eq), and 4-dimethylaminopyridine (DMAP; 0.5 eq) are allowed to react with M30 (1 eq) in dry dimethylformamide (DMF) at room temperature for 24 h. The reaction is filtered and the DMF is removed in vacuo. The residue is dissolved in ethyl acetate and washed with water and brine. The organic layer is dried over magnesium sulfate and concentrated in vacuo. Purification is carried out by column chromatography. In the case of aspartic and glutamic acids, the t-butyl protected beta and gamma carboxylic acids, respectively, are utilized. The purified products are treated with trifluoroacetic acid (TFA): dichloromethane (DCM) [1:1]. After 4 h the solvents are removed in vacuo and the residues reconstituted with water and lyophilized.

In this way the following amino acid esters of M30 can be prepared, having at the 8-position the groups: —$OCOCH_2$ ($NH_2$), —$OCOCH(NH_2)CH_3$, —$OCOCH(NH_2)CH_2OH$, —$OCOCH(NH_2)CH(OH)CH_3$, —$OCOCH(NH_2)CH_2SH$, —$OCOCH(NH_2)CH_2CONH_2$, —$OCOCH(NH_2)$ $CH_2CH_2CONH_2$, —$OCOCH(NH_2)CH(CH_3)_2$, —$OCOCH(NH_2)CH_2CH(CH_3)_2$, —$OCOCH(NH_2)CH(CH_3)CH_2CH_3$, —$OCOCH(NH_2)CH_2Ph$, —$OCOCH(NH_2)CH_2(4-OHPh)$, —$OCOCH(NH_2)CH_2CH_2SCH_3$, —$OCOCH(NH_2)$ $CH_2CH_2CH_2CH_2NH_2$, —$OCOCH(NH_2)CH_2$—$CO_2H$, —$OCOCH(NH_2)CH_2CH_2CO_2H$, —$OCOCH(NH_2)$ $CH_2CH_2CH_2NHC(NH)NH_2$, —$OCOCH(NH_2)CH_2(3$-indolyl), —$OCOCH(NH_2)CH_2(4$-imidazolyl), and —OCO(2-pyrrolidinyl).

Example 4

Syntheses of Ethers of M30

The syntheses of ether derivatives of M30 are described herein below:

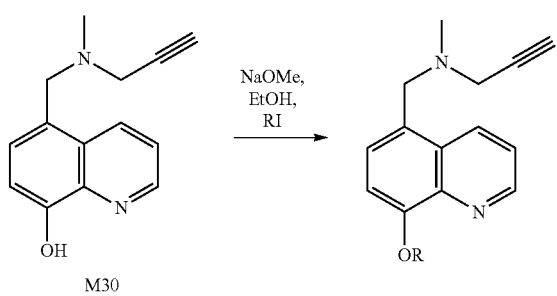

A solution of M30 in anhydrous ethanol is treated with 1.1 eq of sodium methoxide. After 10 min, 1.2 eq of the corresponding alkyl iodide in ethanol is added. The solution is refluxed for 1 h. The solution is allowed to cool, whereupon water is added and the resulting solution is cooled with an ice bath. The resulting crystalline product is collected by filtration.

In this way the following ethers of M30 can be prepared, having at the 8-position the groups: —$OCH_3$, —$OCH_2CH_3$, —$OCH_2CH_2CH_3$, —$OCH_2CH_2CH_2CH_3$, —$OCH_2CN$, $OCH_2CH(CH_3)_2$, —$OCH_2CO_2CH_3$, —$OCH_2CO_2H$, —$OCH_2CON(CH_3)_2$, —$OCH_2C(CH_3)_3$, —$OCH_2CH_2OCH_3$, —$OCH_2CH_2OH$, —$OCH_2OCH_2CH_2CH_3$, —$OCH_2CH_2CH_2OCH_3$, —$OCH_2OCH_3$, and —$OCH_2CH_2CH_2OH$.

Example 5

Synthesis of O-Methyl M30

The synthesis of O-Methyl M30 (ether derivative of M30) hydrochloride is described herein below:

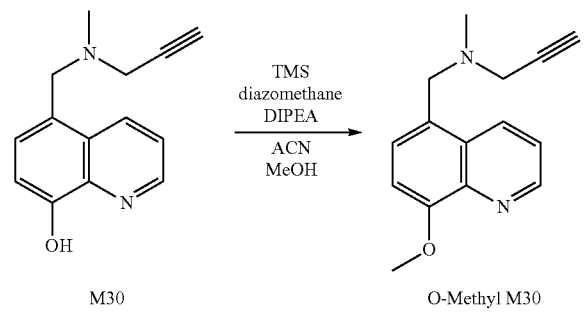

Trimethylsilyl (TMS)diazomethane (4.2 mL, 8.4 mmol, 5 eq) was added to a solution of M30 (500 mg, 1.7 mmol), DIPEA (1.0 mL, 5.9 mmol, 3.5 eq), anhydrous acetonitrile (ACN; 18 mL), and anhydrous MeOH (2.0 mL). The reaction was stirred at room temperature overnight. The volatiles were evaporated and the resulting residue was purified on silica gel with 50-100% ethyl acetate in hexanes (mixture of isomers). Product fractions were pooled and concentrated to give a yellow oil that was dissolved in dichloromethane (DCM) and treated with 4 M HCl in dioxane (0.4 mL). The solution was concentrated and dried under vacuum at room temperature: $^1$H NMR (400 MHz, $D_2O$, δ) 9.32 (d, J=8.8 Hz, 1H), 9.13 (d, J=6.0 Hz, 1H), 8.20 (dd, J=8.8 and 5.2 Hz, 1H), 8.13 (d, J=8.0 Hz, 1H), 7.64 (d, J=8.0 Hz, 1H), 5.01 (s, 2H), 4.23 (s, 3H), 4.11 (d, J=2.4 Hz, 2H), 3.26 (t, J=2.4 Hz, 1H), 3.01 (s, 3H); Mass spectrum, calculated for $C_{15}H_{16}N_2O$ m/z $[M+H]^+$= 241.13, found $[M+H]^+$=241.1.

Example 6

Syntheses of Carbonates of M30

The syntheses of carbonates of M30 are described herein below:

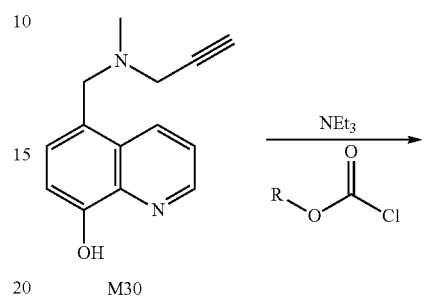

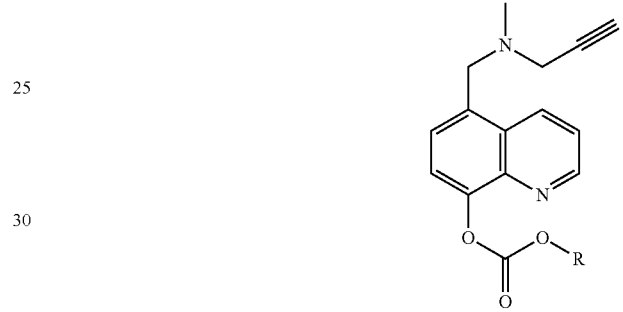

A solution of 1 eq M30 and 1.1 eq TEA in THF is treated by dropwise addition under a nitrogen atmosphere with a solution of 1 eq of the corresponding chloroformate (e.g., for R=$CH_3$, methyl chloroformate) in THF. The resulting solution is washed with aqueous sodium bicarbonate, dried with magnesium sulfate and evaporated. The crude product is purified by crystallization or by column chromatography.

In this way the following carbonates of M30 can be prepared, having at the 8-position the groups: —$OCOOCH_3$, —$OCOOCH_2CH_3$, —$OCOOCH_2CH_2CH_3$, —$OCOO(CH_2)_3CH_3$, —$OCOO(CH_2)_4CH_3$, —$OCOO(CH_2)_7CH_3$, —$OCOOCH_2CH(CH_3)_2$, —$OCOOCH_2Cl$, —$OCOOCH_2CH_2Cl$, —$OCOOCHClCH_3$, —$OCOOCH_2CCl_3$, —$OCOOCH_2CH_2F$, —$OCOOCH_2CF_3$, —$OCOOCH_2CH_2OCH_3$, —$OCOOCH=CH_2$, —$OCOOCH(CH_3)=CH_2$, —$OCOOCH_2CH=CH_2$, —$OCOOCH_2C≡CH$, —$OCOOCH_2CH_2C≡CH$, —OCOOcyclopentyl, —OCOOcyclohexyl, —OCOO(4-toluoyl), —OCOO(4-methoxyphenyl), —OCOO(4-fluorophenyl), —OCOO(4-nitrophenyl), —OCOO(4-nitrobenzyl), and —OCOO(2-isopropyl-5-methylcyclohexylmethyl)

Example 7

Syntheses of Acyloxymethyl Derivatives of M30

The syntheses of acyloxymethyl derivatives of M30 are described herein below:

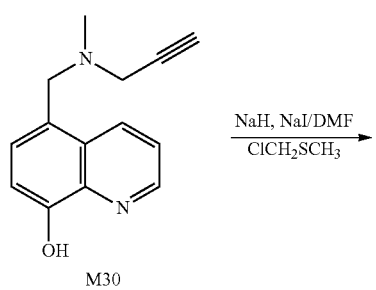

M30

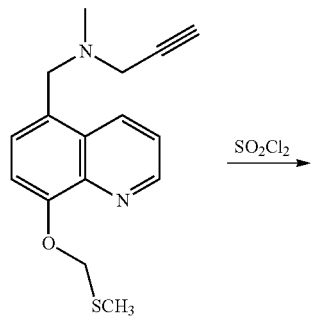

B

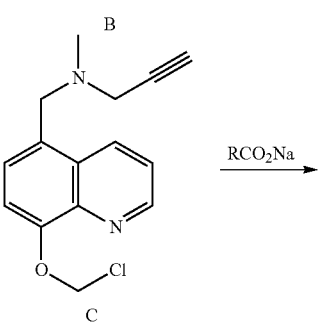

C

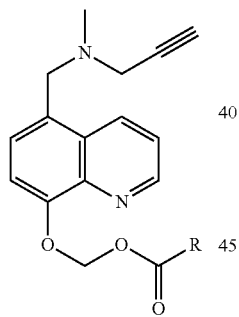

Using the procedure of Skjaeret and Benneche (ARKIVOC, 2001, 16-25), M30 in DMF is added to 1.1 eq of sodium hydride and 1 eq of sodium iodide at 0° C. under $N_2$. After stirring for 15 min 1.3 eq of chloromethyl methyl sulfide is added dropwise. The mixture is stirred for 10 h at ambient temperature, ice/water is added and the product is extracted with diethyl ether, dried ($MgSO_4$), and evaporated. The crude product B (as presented above) is purified by distillation, recrystallization, or flash chromatography Compound B is dissolved in DCM and cooled to 0° C. under $N_2$ and treated by dropwise addition with 1 eq of sulfuryl chloride in DCM. The mixture is stirred for 10 min before it is evaporated under reduced pressure. The crude product C (as presented above) is then dissolved in THF and treated with 1.1 eq of the sodium salt of the appropriate carboxylic acid in THF. After 3 h the mixture is poured into ice water, the mixture is extracted with ethyl acetate, the combined extracts are dried ($MgSO_4$), and evaporated. The crude acyloxymethyl compound is purified by distillation, recrystallization, or flash chromatography.

In this way the following acyloxymethyl derivatives of M30 can be prepared, having at the 8-position the groups: —$OCH_2OCOCH_3$, —$OCH_2OCOCH_2CH_3$, —$OCH_2OCOCH(CH_3)CH_2CH_2CH_3$, —$OCH_2OCOCH_2CH(CH_3)_2$, —$OCH_2OCOCH_2Cl$, —$OCH_2OCOCH_2OCH_3$, —$OCH_2OCOCH_2CH_2OCH_2CH_3$, —$OCH_2OCOCH=CH_2$, —$OCH_2OCOC(CH_3)=CH_2$, —$OCH_2OCOCH=CHCH_3$, —$OCH_2OCOCH=CHPh$, —$OCH_2OCOCH_2CH_2CH=CH_2$, —$OCH_2OCOCH=C(CH_3)_2$, —$OCH_2OCOCF_3$, —$OCH_2OCOCH_2CO_2CH_3$, —$OCH_2OCO$(4-methoxyphenyl), —$OCH_2OCO$(2-thienyl), $OCH_2OCO$(2-furyl), —$OCH_2OCO$cyclopropyl, —$OCH_2OCO$cyclopentyl, —$OCH_2OCO$(5-methylisoxazolyl), and —$OCH_2OCO$(2-chloropyrid-5-yl).

Example 8

Synthesis of 7-methyl-5-[(methyl-2-propyn-1-ylamino)methyl]-8-quinolinol, also known as 5-[N-methyl-N-propargyl(amino)methyl]-7-methyl-quinolin-8-ol, (Herein Designated as Compound 1)

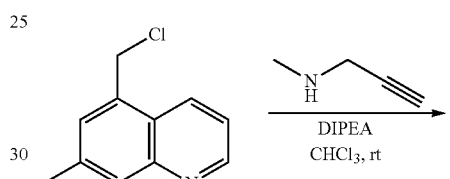

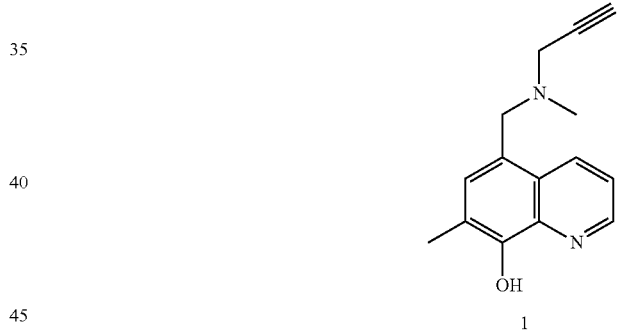

1

The synthesis is identical to that described in Example 1 for the synthesis of M30 employing 7-methyl-8-quinolinol instead of 8-quinolinol as the starting material.

Example 9

Synthesis of 7-fluoro-5-[(methyl-2-propyn-1-ylamino)methyl]-8-quinolinol also known as 5-[N-methyl-N-propargyl(amino)methyl]-7-fluoro-quinolin-8-ol (Herein Designated as Compound 2)

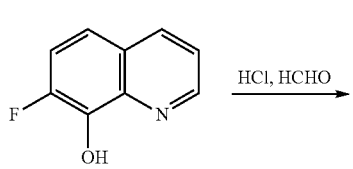

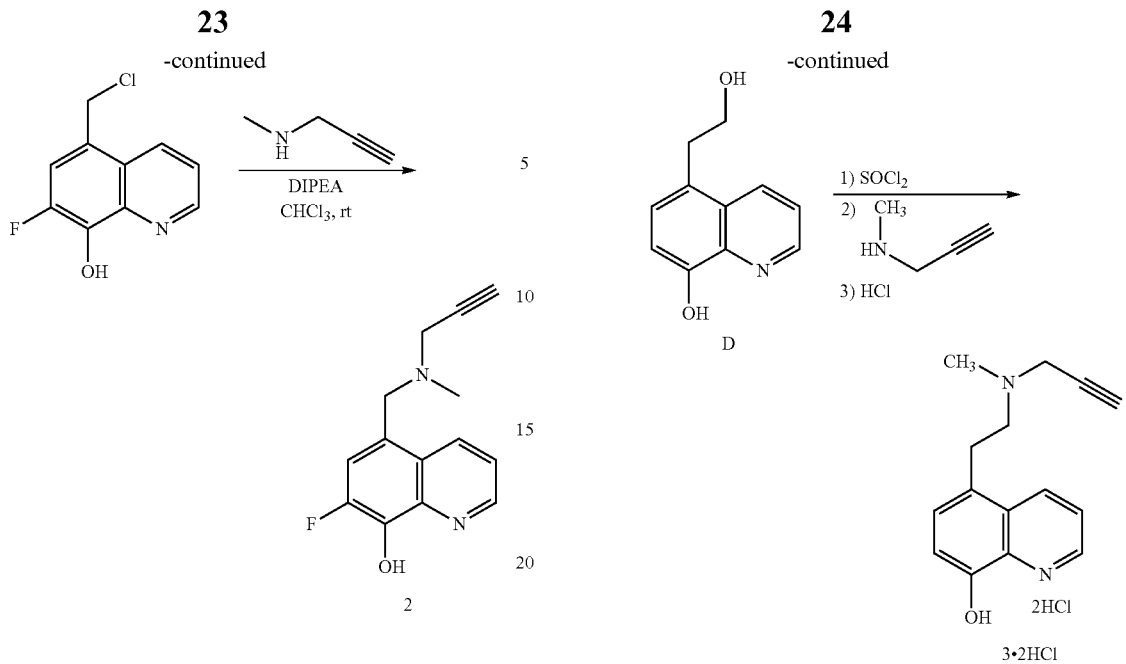

The synthesis is identical to that described in Example 1 for the synthesis of M30 employing 7-fluoro-8-quinolinol instead of 8-quinolinol as the starting material.

Example 10

Synthesis of 5-[2-(methyl-2-propyn-1ylamino)ethyl]-8-quinolinol dihydrochloride also known as 5-[N-methyl-N-propargyl(aminoethyl)]-quinolin-8-ol dihydrochloride (Herein Designated as Compound 3 dihydrochloride)

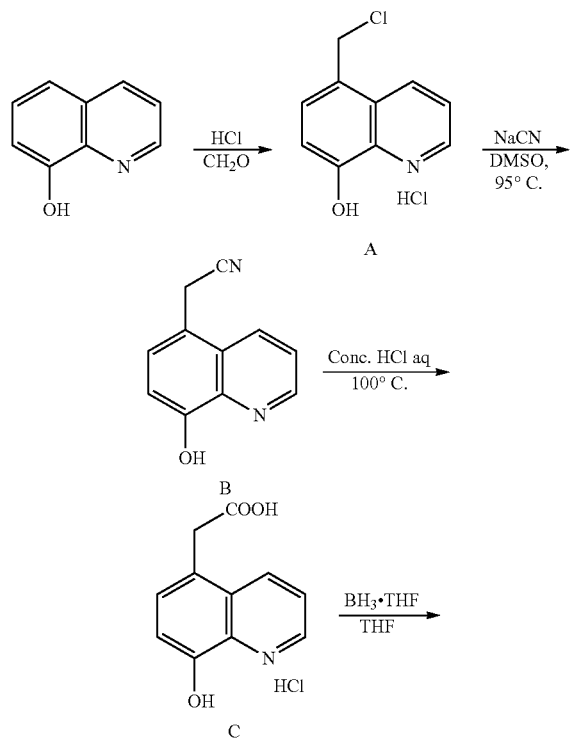

Hydrogen chloride gas was bubbled through a mixture of 8-quinolinol (20 g, 138 mmol), aqueous formaldehyde (37%, 25 mL), and concentrated hydrochloric acid (37%, 25 mL) at 0° C. for 6 hours with stiffing. The stirring was stopped and the reaction mixture reached room temperature overnight. The resulting solid was filtered and dried under vacuum at room temperature to afford compound A as a yellow solid.

A solution of compound A (1.5 g, 6.6 mmol, 5 eq) in anhydrous dimethyl sulfoxide (DMSO; 17 mL) at 90° C. was slowly poured into a solution of sodium cyanide (NaCN; 1.6 g, 33 mmol) in anhydrous DMSO (25 mL) at 95° C. The reaction was stirred at 90° C., under argon, for 1 hour, and then allowed to cool to room temperature. The reaction was acidified by dropwise addition of concentrated hydrochloric acid followed by neutralization with aqueous sodium hydroxide. The mixture was chilled to 0° C., the resulting precipitate filtered, rinsed with water, and dried. The solid obtained was recrystallized from benzene, rinsed with hexanes, and dried under vacuum to provide compound B as a brown solid.

A suspension of compound B (1.0 g, 5.4 mmol) in concentrated hydrochloric acid (37%, 20 mL) was heated to 100° C. with stirring for 3 hours. The volatiles were evaporated and the resulting solid, compound C, was dried under vacuum at room temperature overnight.

Borane-THF complex (1 M in THF, 20 mL) was added slowly to a suspension of compound C (1.1 g, 4.07 mmol) in anhydrous THF (10 mL) at 0° C. with stirring under argon. The reaction was allowed to warm to room temperature overnight, then chilled to 0° C., quenched with water (10 mL), and made slightly basic with aqueous sodium bicarbonate solution. The volatiles were evaporated and the resulting solid triturated with 20% MeOH in DCM. The mixture was filtered and the filtrate concentrated. The resulting residue was purified on silica gel with 20-80% ethyl acetate in hexanes. Pure fractions by LC/MS of compound D were pooled and concentrated and dried under vacuum at room temperature overnight.

Thionyl chloride was added to a solution of compound D (100 mg, 0.53 mmol) in anhydrous DCM (3 mL) and the mixture was heated to 60° C. with stiffing for 3 hours. The mixture was evaporated to dryness and the resulting solid dissolved in anhydrous DMF (5 mL). Sodium iodide (79 mg, 0.53 mmol, 1 eq), DIPEA (0.92 mL, 5.3 mmol, 10 eq), and N-methylpropargyl amine (1.32 mL, 16 mmol, 30 eq) were added. The reaction mixture was heated to 95° C. for 4 hours then allowed to cool to room temperature. The volatiles were evaporated and the resulting residue was purified on silica gel with 0-10% MeOH in DCM. Product fractions were concentrated to give yellow oil that was dissolved in DCM (2 mL) and was treated with 4 M HCl in dioxane (1 mL). The precipitate was filtered and dried under vacuum at 60° C. affording 5-[2-(methyl-2-propyn-1-ylamino)ethyl]-8-quinolinol, herein designated as compound 3 dihydrochloride: $^1$H NMR (400 MHz, CD$_3$OD, δ) 9.40 (dd, J=8.8 and 1.2 Hz, 1H), 9.09 (dd, J=5.2 and 1.2 Hz, 1H), 8.17 (dd, J=8.8 and 5.2 Hz, 1H), 7.80 (d, J=8.0 Hz, 1H), 7.45 (d, J=8.0 Hz, 1H), 4.30 (s, 2H), 3.57 (m, 4H), 3.46 (app t, J=2.8 and 2.4 Hz, 1H), 3.13 (s, 3H); Mass spectrum, calculated for C$_{15}$H$_{16}$N$_2$O m/z [M+H]$^+$= 241.13, found [M+H]$^+$=241.1.

Example 11

Alternative synthesis of 5-[2-(methyl-2-propyn-1-ylamino)ethyl]-8-quinolinol (compound 3) and 5-[2-(methyl-2-propyn-1-ylamino)ethyl]-8-quinolinol citrate salt (3 citrate)

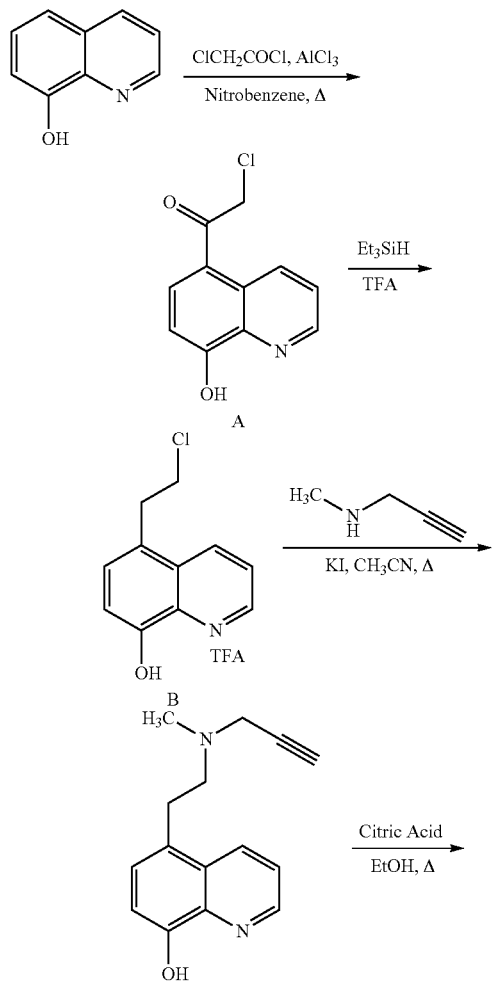

3

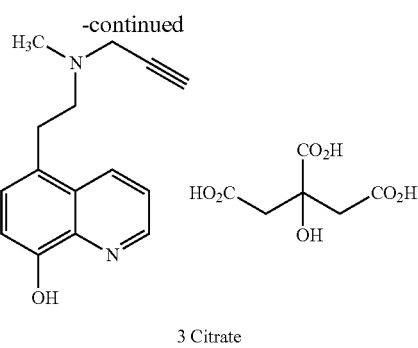

3 Citrate

To a stirred solution of 8-quinolinol (97.0 g, 0.67 mol) in nitrobenzene (460 mL) was added chloroacetyl chloride (55.8 mL, 0.701 mol) at 0° C. under argon (suspension formed). Aluminum chloride (160 g, 1.20 mol) was added in portions upon which the suspension became clear. The reaction mixture was heated at 100° C. for 35 h (hours, or hour). The reaction mixture was cooled to rt (room temperature) and poured into an ice cold mixture of 6 N HCl (450 mL), ice (600 g), and methyl t-butyl ether (MTBE, 800 mL). The yellow precipitate was filtered, washed with MTBE (~500 mL), and dried. The solid obtained (aluminum complex) was added to 12 N HCl (200 mL) and stirred at rt for 3 days. The mixture was filtered and the solids obtained were washed with ethyl acetate then stirred with 10% NaOAc aqueous solution (enough to make pH=6, ~2 L), providing a green suspension that was filtered. The green solids obtained were dissolved into dichloromethane (DCM, 1.8 L), dried (MgSO$_4$), and filtered. The volume was reduced to ~500 mL providing a yellow solid that was filtered, washed with MTBE, and dried providing 58.5 g (38.5%) of compound A as a yellow solid.

To compound A (27.3 g, 0.123 mol) under argon chilled to 0° C. was added trifluoroacetic acid (270 g) followed by triethylsilane (196 mL, 1.23 mol). The reaction was warmed to rt then heated at 60° C. for 22 h. The mixture was cooled to rt and concentrated and dried in vacuo at 34-40° C. The clear oil was decanted from the dark product residue and triturated with ether. The solid obtained was filtered, rinsed with ether, and dried providing 34.2 g (86.4%) compound B as a yellow solid.

To a suspension of compound B (12.0 g, 37.3 mmol) in anhydrous acetonitrile (130 mL) in a sealable reaction tube was added KI (6.10 g, 37.3 mmol) and N-methylpropargyl amine (15 g, 220 mmol). The tube was sealed and the mixture was heated at 100° C. for 36 h. After cooling to rt, the mixture was concentrated in vacuo and partitioned between DCM and saturated NaHCO$_3$ (250 mL). The aqueous layer was extracted twice with DCM. The combined organic extracts were washed with brine and concentrated in vacuo. The residue obtained was purified by chromatography (silica gel, 1% NH$_4$OH in ethyl acetate/hexanes, 50-100%) providing compound 3 (4.4 g, 50%) as a yellow solid: $^1$H NMR (400 MHz, DMSO-d$_6$, δ) 9.54 (s, 1H), 8.84 (dd, J=4.0 and 1.6 Hz, 1H), 8.46 (dd, J=8.4 and 1.6 Hz, 1H), 7.58 (dd, J=8.4 and 4.0 Hz, 1H), 7.32 (d, J=8.0 Hz, 1H), 7.00 (d, J=8.0 Hz, 1H), 3.40 (d, J=2.4 Hz, 2H), 3.28 (s, 1H), 3.10 (m, 2H), 2.61 (m, 2H), 2.29 (s, 3H).

A mixture of compound 3 (3.00 g, 12.5 mmol) and citric acid (2.40 g, 12.5 mmol) in EtOH (7 mL) was heated at 65-75° C. until a clear solution was achieved (~1 h). The reaction mixture was cooled to rt gradually using a warm water bath allowing the salt to slowly form. The solvent was decanted and the solids were dried under vacuum to afford 5.16 g (95%) of compound 3 citrate (1:1) as a light brown solid: $^1$H NMR (400 MHz, DMSO-d$_6$, δ) 9.58 (s, 1H), 8.85 (dd, J=4.0 and 1.6 Hz, 1H), 8.47 (dd, J=8.4 and 1.6 Hz, 1H), 7.59 (dd, J=8.4 and 4.0 Hz, 1H), 7.32 (d, J=8.0 Hz, 1H), 7.01 (d, J=8.0 Hz, 1H), 3.54 (d, J=2.4 Hz, 2H), 3.25 (t, J=2.4 Hz, 1H), 3.11 (m, 2H), 2.75 (overlapping d and m, 4H), 2.63 (d, J=15.2 Hz, 2H), 2.50 (s, 3H); Mass spectrum, calculated for $C_{15}H_{16}N_2O$ m/z+[M+H]$^+$=241.13, found [M+H]$^+$=241.1.

Example 12

Synthesis of 5-[3-(methyl-2-propyn-1-ylamino)propyl]-8-quinolinol hydrochloride also known as 5-[N-methyl-N-propargyl(aminopropyl)]-quinolin-8-ol (compound 4) dihydrochloride

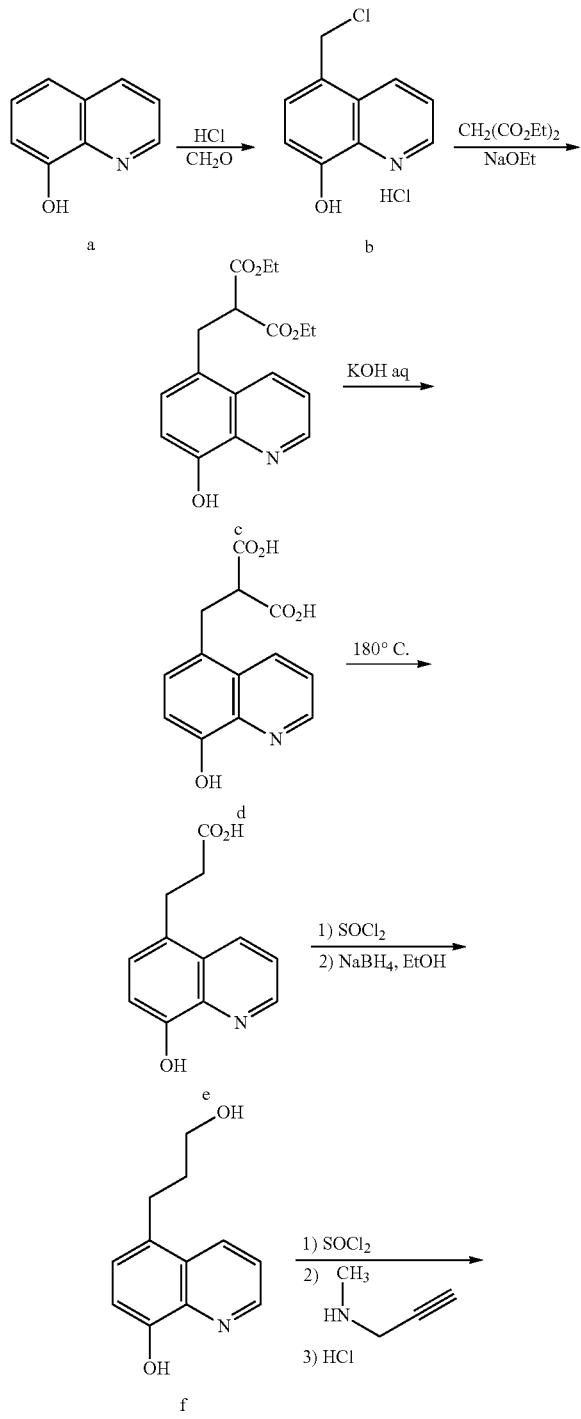

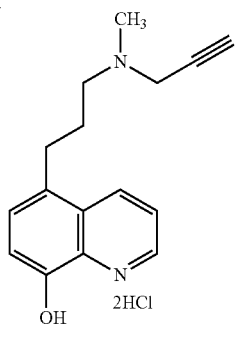

Hydrogen chloride gas was bubbled through a mixture of 8-quinolinol (compound a; 20 g, 138 mmol), aqueous formaldehyde (25 mL), and concentrated hydrochloric acid (37%, 25 mL) at 0° C. for 6 hours with stirring. The stirring was stopped and the reaction reached room temperature overnight. The resulting yellow solid was filtered and dried under vacuum at room temperature affording compound b.

Diethyl malonate (10 mL, 66 mmol, 5 eq) was added dropwise to a solution of sodium ethoxide (14.7 mL of 21 wt %, 39 mmol, 3 eq) in anhydrous EtOH (15 mL) at 0° C. with stirring. Compound b (3.0 g, 13 mmol) was added and the reaction mixture was allowed to warm to room temperature for 2 hours. The solvent was evaporated in vacuo and the resulting residue dissolved with water and ethyl acetate. The layers were separated and the aqueous layer extracted twice with ethyl acetate. The combined organic layers were washed twice with water, once with brine, and concentrated in vacuo. The material was purified by chromatography on silica gel with 10-30% ethyl acetate in hexanes. Product fractions were pooled and concentrated in vacuo and the resulting white solid dried under vacuum affording compound c.

A solution of potassium hydroxide (9.3 g) in water (15 mL) was added to compound c (3.0 g, 9.46 mmol) and the reaction mixture was stirred at room temperature over the weekend. The pH of the reaction was adjusted to between 4 and 5 with concentrated HCl and diluted with water (20 mL). The resulting yellow precipitate was filtered, rinsed with water, and dried under vacuum affording compound d.

Compound d was heated to 180° C., vented to a bubbler, for 1 hour and then allowed to cool to room temperature under argon, yielding compound e.

A suspension of compound e (1.0 g, 4.6 mmol) in thionyl chloride (9.0 mL) was stirred at room temperature for 0.5 h and then the volatiles were evaporated in vacuo. The resulting yellow solid was stirred with anhydrous DCM (5 mL) at 0° C. and then a solution of sodium borohydride (0.52 g, 14 mmol, 3 eq) in anhydrous EtOH (9 mL) was added. The reaction mixture was allowed to warm to room temperature for 1 hour then quenched with water. The aqueous mixture was extracted three times with 10% MeOH in DCM. The combined organic layers were washed with water, brine, and dried over anhydrous sodium sulfate. The material was purified by chromatography on silica gel with 20-60% ethyl acetate in hexanes. Product fractions were concentrated in vacuo and the resulting white solid dried under vacuum yielding compound f.

Thionyl chloride (3 mL) was added to compound f (100 mg, 0.49 mmol) and the suspension heated to 40-50° C. with stirring for 4 hours. The mixture was evaporated to dryness in vacuo and the resulting solid stirred with anhydrous ACN (2.5 mL). Sodium iodide (74 mg, 0.49 mmol, 1 eq), TEA (0.69 mL, 4.9 mmol, 10 eq), and N-methylpropargyl amine (1.23 mL, 15 mmol, 30 eq) were added. The reaction mixture was heated to 70° C. overnight then allowed to cool to room temperature. The volatiles were evaporated in vacuo and the resulting residue was purified on silica gel with 0-10% MeOH in DCM. Product fractions were concentrated in vacuo to give yellow oil that was dissolved in DCM (2 mL) and treated with 4 M HCl in dioxane (0.5 mL). The precipitate was filtered, rinsed with DCM, and dried under vacuum at room temperature yielding 5-[3-(methyl-2-propyn-1-ylamino)propyl]-8-quinolinol dihydrochloride, herein designated as compound 4 dihydrochloride: $^1$H NMR (400 MHz, CD$_3$OD, δ) 9.39 (dd, J=8.8 and 1.2 Hz, 1H), 9.07 (dd, J=5.6 and 1.2 Hz, 1H), 8.14 (dd, J=8.8 and 5.6 Hz, 1H), 7.74 (d, J=8.0 Hz, 1H), 7.43 (d, J=8.0 Hz, 1H), 4.15 (br m, 2H), 3.44-3.35 (br m, 2H), 3.39 (app t, J=2.8 and 2.4 Hz, 1H), 3.25 (app t, J=8.0 and 7.6 Hz, 2H), 2.97 (s, 3H), 2.16 (m, 2H); Mass spectrum, calculated for C$_{16}$H$_{18}$N$_2$O m/z [M+H]$^+$=255.15, found [M+H]$^+$=255.1.

Example 13

Synthesis of 5-[1-(methyl-2-propyn-1-ylamino)ethyl]-8-quinolinol hydrochloride also known as 5-[N-methyl-N-propargyl(1-aminoethyl)]-8-quinolinol (compound 5) dihydrochloride

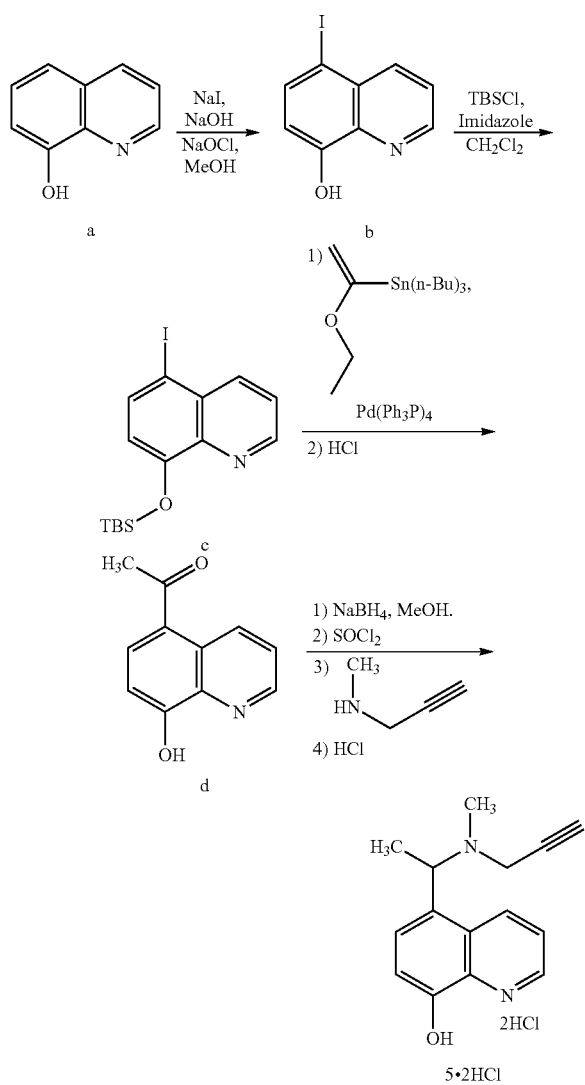

A solution of 8-quinolinol (15 g, 103 mmol), sodium iodide (15.5 g, 103 mmol, 1 eq) and sodium hydroxide (4.1 g, 103 mmol, 1 eq) in methanol (450 mL) was purged with nitrogen for 30 min and then chilled to −30° C. Sodium hypochlorite (5% in water) (149 mL) was added dropwise over 50 min and the reaction mixture stirred for additional 1 h at −30° C. The cold bath was removed and the reaction neutralized with 10% aqueous hydrogen chloride. The resulting solids were filtered, rinsed with water, and dried to give a solid that was re-crystallized from methanol and water providing compound b.

To a solution of compound b (7.5 g, 28 mmol) in anhydrous dichloromethane (DCM) under argon was added imidazole (3.0 g, 44 mmol, 1.5 eq) and tert-butyldimethylsilyl chloride (TBSCl; 6.9 g, 46 mmol, 1.6 eq). The reaction mixture was stirred at room temperature for 3 days. The reaction mixture was diluted with DCM and the organics were washed with saturated aqueous ammonium chloride, water, brine, and then were dried over anhydrous sodium sulfate. The solution was filtered and concentrated. The resulting residue was purified on silica gel with 0-3% ethyl acetate in hexanes. Pure fractions of c were pooled, concentrated, and dried under vacuum at room temperature.

A solution of compound c (6.2 g, 16 mmol) and tributyl(1-ethoxyvinyl)tin (6.5 mL, 19 mmol, 1.2 eq) in anhydrous toluene was purged with argon for 5 min. Tetrakis-(triphenylphosphine)palladium(0) (0.93 g, 0.80 mmol, 0.05 eq) was added and the reaction mixture was heated to 105-112° C. for 2 days in a sealed tube. The reaction mixture was filtered through celite, rinsed with toluene and concentrated. The resulting residue was taken up in THF (50 mL) and 3 N HCl (36 mL) and stirred at room temperature overnight. The reaction was adjusted to pH=8 with solid sodium bicarbonate and extracted three times with DCM. The combined organic layers were dried over anhydrous sodium sulfate, filtered, and concentrated. The material was purified by chromatography on silica gel with 0-3% MeOH in DCM. The MeOH used for chromatography contained 2% of an aqueous ammonium hydroxide. Product fractions were concentrated and the resulting solid d was dried under vacuum.

To a solution of compound d (300 mg, 1.6 mmol) in anhydrous MeOH at 0° C. under argon was added sodium borohydride (303 mg, 8.0 mmol, 5 eq). The reaction mixture was allowed to warm to room temperature and stirred for 0.5 h. The reaction mixture was quenched with water, the pH was adjusted to between 7 and 8, and the volatiles were evaporated. The resulting residue was tritrated with 20% MeOH in DCM, the solids were filtered, and then the filtrate was concentrated and dried under vacuum. The solid obtained was stirred with thionyl chloride (5 mL) at 55° C. for 1.5 h and then the volatiles were evaporated. The resulting solid was stirred with anhydrous chloroform (12 mL) at 0° C. N-Methylpropargyl amine (1.1 mL, 16 mmol, 10 eq) was added dropwise and the reaction mixture was stirred at room temperature overnight under argon. The volatiles were evaporated and the resulting residue was triturated with DCM (20 mL). The precipitate was filtered and the filtrate was dried over anhydrous sodium sulfate. The DCM solution was filtered and treated with 4 M HCl in dioxane (0.6 mL). The precipitate was filtered and dried under vacuum to give a solid that was triturated with toluene, ACN, and chloroform. The solid was filtered and dried under vacuum overnight allowing 5-[1-(methyl-2-propyn-1-ylamino)ethyl]-8-quinolinol dihydrochloride, herein designated compound 5 dihydrochloride: $^1$H NMR (400 MHz, D$_2$O, δ) 9.40 (d, J=8.8 Hz, 1H), 9.11 (dd, J=5.2 and 1.2 Hz, 1H), 8.17 (dd, J=8.8 and 5.2 Hz, 1H), 6.06 (d, J=8.4 Hz, 1H), 7.60 (d, J=8.4 Hz, 1H), 5.65, (q, J=6.8 Hz, 1H), 4.11 (br d, J=15.6 Hz, 1H), 4.00 (m, 1H), 3.19 (app t, J=2.8 and 2.4 Hz, 1H), 3.00 (bs s, 3H), 1.90 (d, J=6.8 Hz, 3H); Mass spectrum, calculated for $C_{15}H_{16}N_2O$ m/z $[M+H]^+=241.13$, found $[M+H]^+=241.1$.

Example 14

Synthesis of 7-methyl-5-[2-(methyl-2-propyn-1-ylamino)ethyl]-8-quinolinol also known as 5-[N-methyl-N-propargyl(aminoethyl)]-7-methyl-8-quinolinol (compound 6)

Synthetic methods to produce the compound 3 homologs substituted at 7-position have been developed. Except for the fluoro analog, all of the analogs can be made available via a common intermediate. The synthetic routes to these analogs are shown in schemes below.

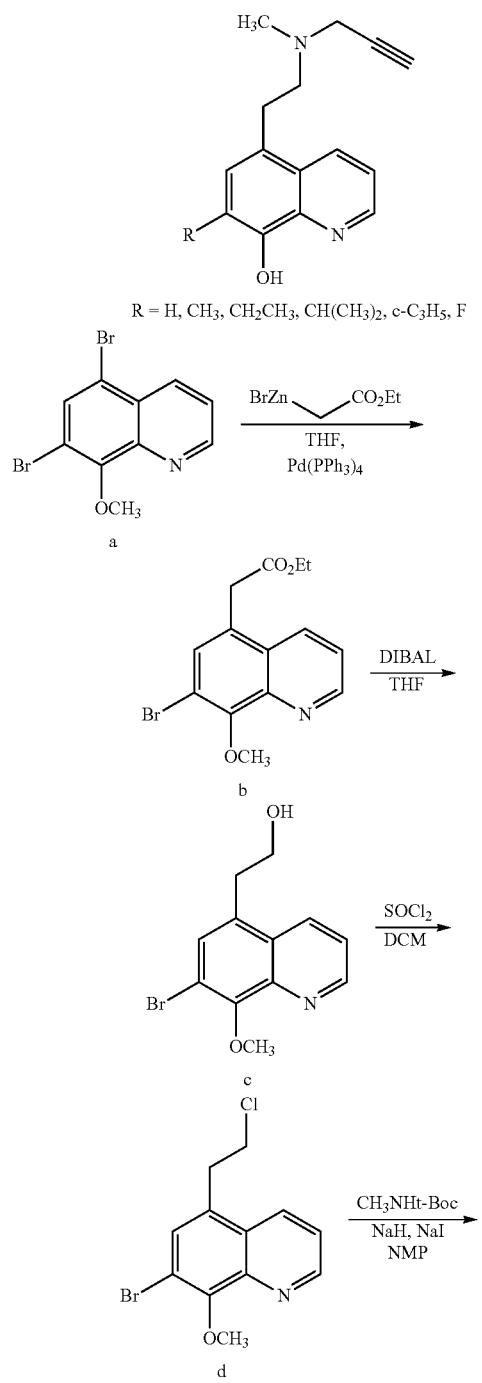

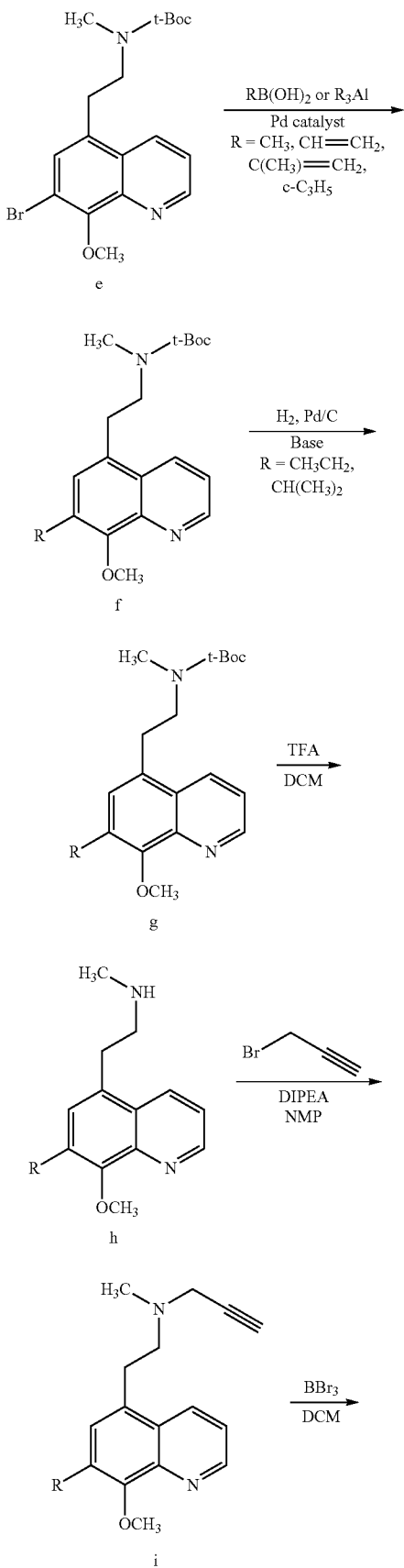

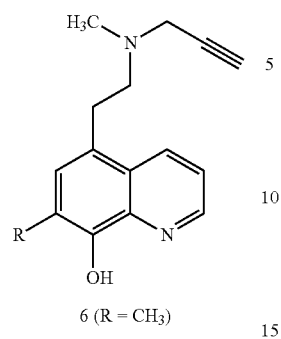

6 (R = CH₃)

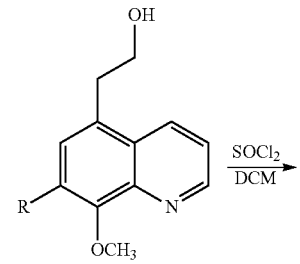

The synthesis starts with a palladium catalyzed coupling of readily available 5,7-dibromo-8-methoxyquinoline (a) with the Reformatsky reagent derived from ethyl bromoacetate. There is literature precedence for formation of the 5-position acetate b versus the 7-position, at least for Suzuki coupling of a with arylboronic acids (*J. Heterocyclic Chem.*, 1995, 32, 1261-1267). Functional group manipulation leads to the common t-Boc protected intermediate amine e. The ethenyl (f, R=CH=CH₂), 2-propenyl (f, R=C(CH₃)=CH₂), and cyclopropyl (f, c-C₃H₅) groups are introduced via Suzuki coupling of e with the appropriate boronic acid while trimethylaluminum catalyzed coupling provides the methyl analog f, R=CH₃ (*Advanced Synthesis and Catalysts*, 2006, 348, 686-690). Reduction of the 2 olefin analogs provides the ethyl (g, R=CH₂—CH₃) and isopropyl (g, R=CH(CH₃)₂) analogs. Removal of the t-Boc group, alkylation with propargyl bromide, and removal of the methyl ether completes the synthesis.

In a similar fashion, the synthesis of the 7-fluoro analog starts from 5-bromo-7-fluoro-8-methoxyquinoline (j), available by NBS bromination of 7-fluoro-8-quinolinol and methylation (*J. Med. Chem.*, 1972, 15, 987-989 and references cited therein). This route can also be used to prepare compounds wherein R is —CH₃, —CH₂CH₃, —CH(CH₃)₂, -c-C₃H₅, or —F starting from 5-bromo-8-methoxyquinoline (j, R=H).

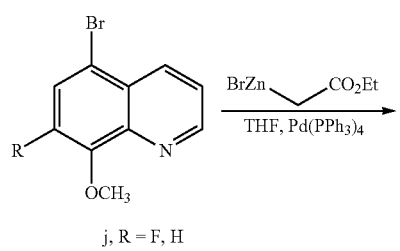

j, R = F, H

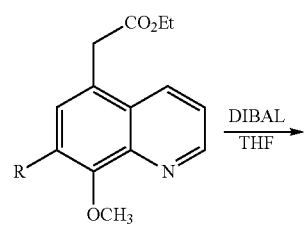

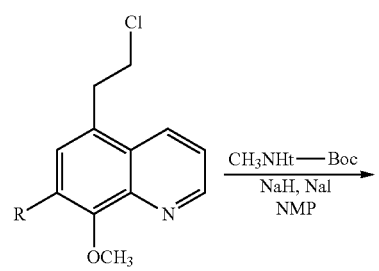

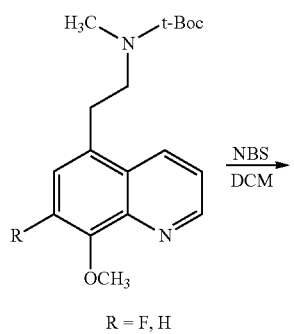

R = F, H

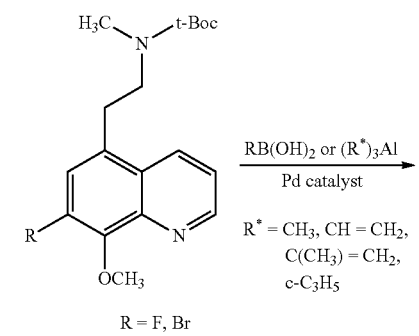

R* = CH₃, CH=CH₂, C(CH₃)=CH₂, c-C₃H₅

R = F, Br

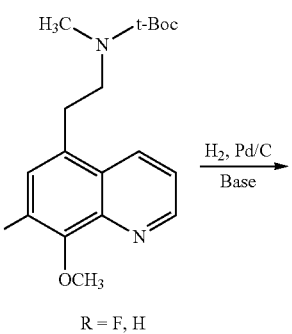

R = F, H

-continued
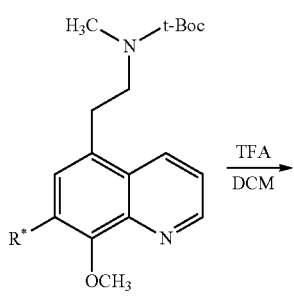
R* = CH₂CH₃, CH(CH₃)₂
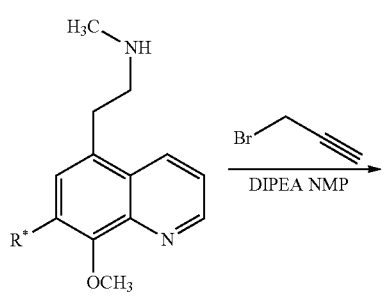
R* = CH₂CH₃, CH(CH₃)₂, c-C₃H₅, F
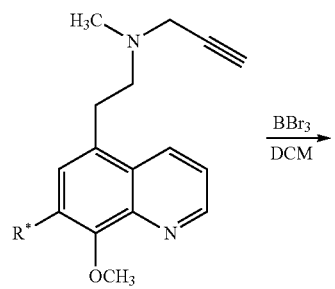
R* = CH₃, CH₂CH₃, CH(CH₃)₂, c-C₃H₅, F
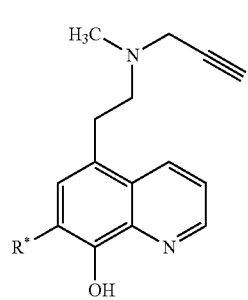
Example 15
Synthesis of 7-cyclopropyl-5-[2-(methyl-2-propyn-1-ylamino)ethyl]-8-quinolinol also known as 5-[N-methyl-N-propargyl(aminoethyl)]-7-cyclopropyl-8-quinolinol (compound 7)
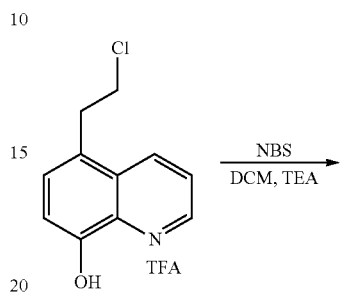
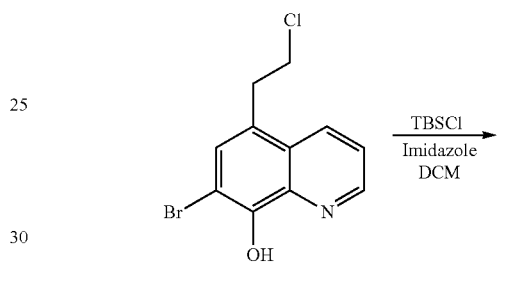
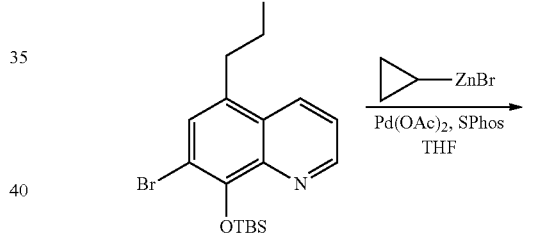
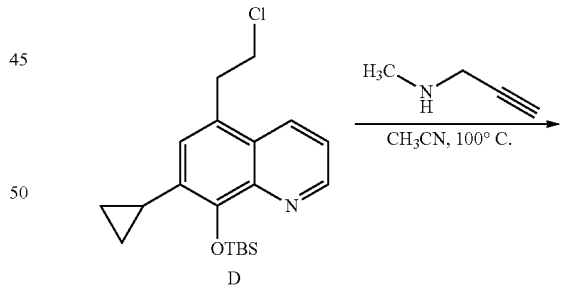
D
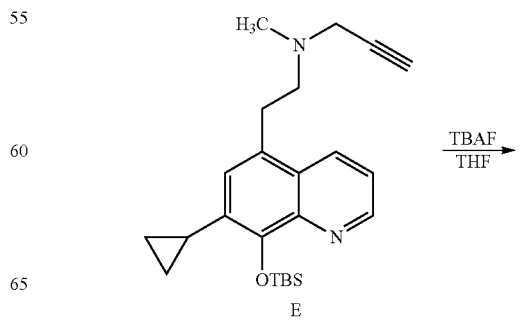
E

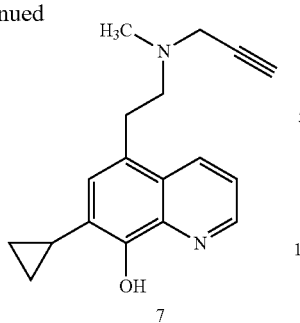

To a stirred suspension of compound A (642 mg, 2.0 mmol, prepared according to the procedure provided in Example 11) in DCM (6 mL) at rt was added triethylamine (0.60 mL, 4.0 mmol). N-Bromosuccinimide (NBS, 416 mg, 2.4 mmol) was added in one portion. The resulting brown suspension was stirred at rt for 2 h. The reaction mixture was diluted with DCM (20 mL) and washed with saturated NaHCO$_3$ and brine. The organic layer was concentrated in vacuo and the residue was purified on silica gel column with 10-30% ethyl acetate/hexanes to give 440 mg (76.9%) of compound B as a white solid.

To a solution of compound B (250 mg, 0.87 mmol) in DCM (5 mL) at rt was added imidazole (178 mg, 2.62 mmol) and t-butyldimethylsilyl chloride (TBSCl, 196 mg, 1.31 mmol). After stirring at rt for 16 h, the reaction mixture was diluted with DCM (20 mL) and washed with brine. The organic layer was concentrated in vacuo and residue obtained was purified on silica gel column with 0-10% ethyl acetate/hexanes providing 300 mg (86.5%) of compound C as a white solid.

Compound C (220 mg, 0.55 mmol), palladium acetate (37 mg, 0.10 mmol) and 2-dicyclohexylphosphino-2',6'-dimethoxybiphenyl (SPhos, 45 mg, 0.20 mmol) were added to a dry vial under argon. The vial was charged with 0.5 M solution cyclopropyl zinc bromide in THF (3.30 mL, 1.65 mmol). The reaction mixture was degassed with argon for 5 min, sealed, and then heated at 60° C. for 2 h. After cooling to rt, the reaction mixture was diluted with ethyl acetate (20 mL) and washed with brine. The organic layer was concentrated in vacuo. The residue obtained was purified on silica gel column with 0-10% ethyl acetate/hexanes providing compound D (178 mg, 90.8%) as a white solid.

To a suspension of compound D (240 mg, 0.66 mmol) and acetonitrile (2.5 mL) in a sealable vial was added N-methylpropargyl amine (365 mg, 5.3 mmol). The vial was sealed and heated at 100° C. for 30 h. The reaction mixture was cooled to rt, concentrated in vacuo, and residue obtained purified on silica gel with 30% ethyl acetate/hexanes providing compound E 180 mg (69.2%) as a white solid.

To a solution of compound E (180 mg, 0.50 mmol) in anhydrous THF (4 mL) was added 1.0 M tetra-n-butylammonium fluoride (TBAF) in THF (2.5 mL, 2.5 mmol). The mixture was stirred at rt for 30 min, and then concentrated in vacuo to a syrup that was purified on silica gel with 50% ethyl acetate/hexanes providing compound 7 (47 mg, 33.5%) as a white solid: $^1$H NMR (400 MHz, CDCl$_3$, δ) 8.74 (dd, J=4.0 and 1.2 Hz, 1H), 8.37 (br s, 1H), 8.32 (d, J=8.4 Hz, 1H), 7.38 (dd, J=8.4 and 4.0 Hz, 1H), 6.89 (s, 1H), 3.48 (br s, 2H), 3.11 (br t, J=7.6 Hz, 2H), 2.71 (br s, 2H), 2.44 (s, 3H), 2.40 (m, 1H), 2.27 (s, 1H), 1.06 (m, 2H), 0.83 (m, 2H); Mass spectrum, calculated for C$_{18}$H$_{21}$N$_2$O m/z [M+H]$^+$=281.16, found [M+H]$^+$=281.0.

Example 16

Synthesis of 7-fluoro-5-[2-(methyl-2-propyn-1-ylamino)ethyl]-8-quinolinol also known as 5-[N-methyl-N-propargyl(aminoethyl)]-7-fluoro-8-quinolinol (compound 8) and 7-fluoro-5-[2-(methyl-2-propyn-1-ylamino)ethyl]-8-quinolinol dihydrochloride (compound 8 2HCl)

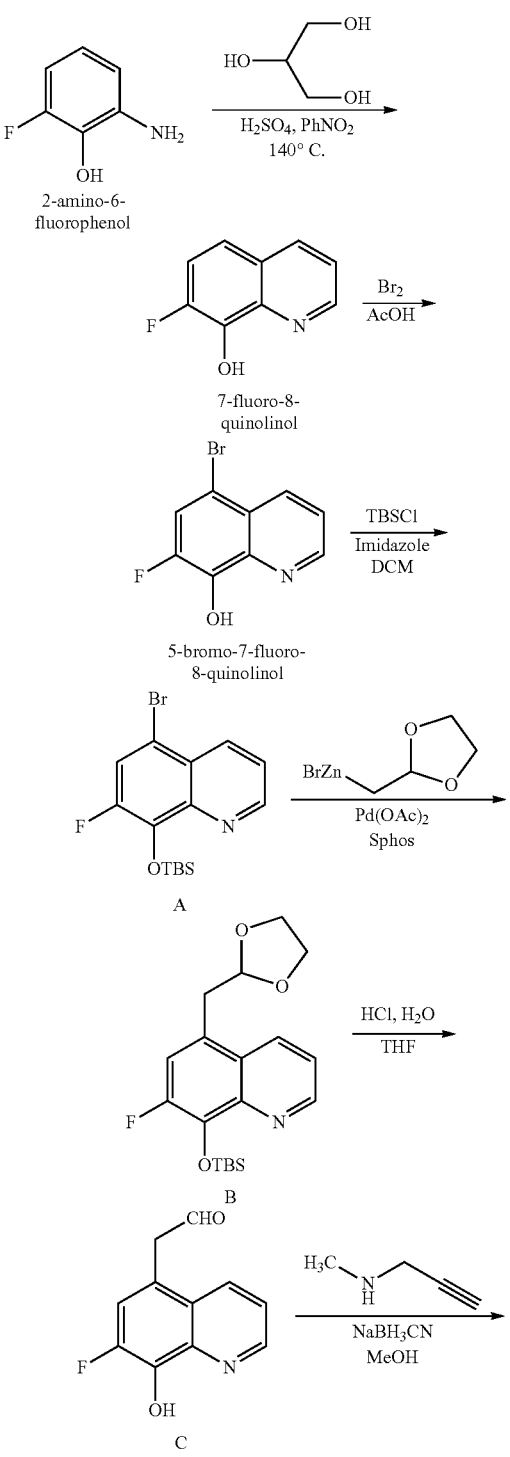

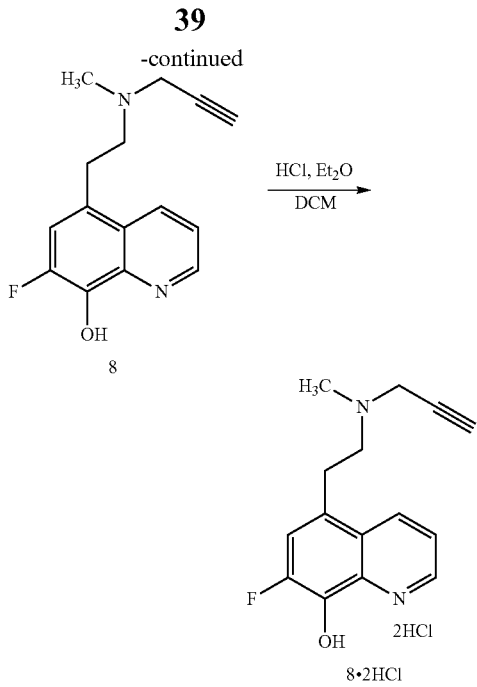

To a solution of 2-amino-6-fluorophenol (4.0 g, 31.6 mmol) and nitrobenzene (20 mL) in a sealable reaction vessel was added in portions sulfuric acid (4.0 mL). Glycerol (12.0 g, 126 mmol) was added in one portion, and the solution turned to dark brown. The vessel was flushed with nitrogen, sealed and heated to 140° C. for 6 h. The reaction mixture was cooled to rt, diluted with 30 mL ice/water mixture, and washed 3 times with methyl t-butyl ether (removes most of the nitrobenzene). The aqueous phase was neutralized to pH=6-7 by slow addition of 6N NaOH. The resulting black precipitate was collected and the water solution was extracted with ethyl acetate 3 times. The organic extracts were combined with the black precipitate, concentrated in vacuo, and purified on silica gel column with 0-10% MeOH/DCM to give 2.67 g (51.7%) of 7-fluoro-8-quinolinol as an off-white solid.

An rt solution of bromine (2.34 g, 14.7 mmol) in acetic acid (10 mL) was slowly added to a solution of 7-fluoro-8-quinolinol (2.0 g, 12.2 mmol) in acetic acid (30 mL). The brown reaction mixture was stirred at rt for 16 h, after which the mixture was quenched with saturated sodium bisulfite solution. The resulting mixture was extracted with methyl t-butyl ether 3 times. The combined organic phases were washed with saturated $NaHCO_3$ and brine, dried over $Na_2SO_4$, and concentrated in vacuo to dryness to give 3.0 g (97.0%) 5-bromo-7-fluoro-8-quinolinol as a green solid.

To an rt solution of 5-bromo-7-fluoro-8-quinolinol (1.12 g, 4.60 mmol) in DCM (20 mL) was added imidazole (680 mg, 10.0 mmol) and TBSCl (900 mg, 6.0 mmol). After 2 h at rt, the reaction mixture was diluted with DCM (60 mL), washed with brine, and concentrated in vacuo. The residue obtained was purified on silica gel column with 0-10% ethyl acetate/hexanes to give 1.50 g (91.5%) of compound A as a white solid. Compound A (1.12 g, 3.14 mmol), palladium acetate (208 mg, 0.62 mmol), and SPhos (254 mg, 0.62 mmol) were charged to a dry vial under nitrogen. To this vial was added 0.5 M (1,3-dioxolan-2-ylmethyl)zinc bromide (10.5 mL, 6.28 mmol) in THF. The reaction mixture was degassed with nitrogen for 5 min. The resulting dark brown mixture was heated to 60° C. for 2 h. The reaction mixture was diluted with ethyl acetate (40 mL) and washed with brine. The organic layer was concentrated in vacuo and the residue obtained purified on silica gel column with 0-50% ethyl acetate/hexanes to give 1.10 g (95.8%) of compound B as a white solid.

To a solution of compound B (1.10 g, 3.0 mmol) in THF (5 mL) was added 3.0 M HCl (25 mL). After 3 h at rt, the reaction mixture was washed with methyl t-butyl ether 3 times. The acidic aqueous phase was neutralized to pH ~7 and extracted with DCM three times. The combined organic phases were washed with brine, dried over $Na_2SO_4$, and concentrated in vacuo to dryness to give 570 mg (92.6%) of compound C as a yellow solid.

To a solution of compound C (102 mg, 0.50 mmol) in methanol (3.0 mL) was added N-methylpropargyl amine (82.5 mg, 1.50 mmol). After stirring at rt for 1 h, sodium cyanoborohydride (62.8 mg, 1.50 mmol) was added in one portion and stirred at rt for 3 h. The reaction mixture was quenched with saturated ammonium hydrochloride and extracted with DCM 3 times. The combined organic extracts were concentrated in vacuo and the residue obtained purified on silica gel with 50-100% ethyl acetate/hexanes providing compound 8 (41 mg, 32%) as a light yellow solid: $^1$H NMR (400 MHz, $CDCl_3$, δ) 8.72 (dd, J=4.0 and 1.2 Hz, 1H), 8.31 (d, J=8.4 Hz, 1H), 7.36 (dd, J=8.4 and 4.0 Hz, 1H), 7.21 (d, $J_{HF}$=12.0 Hz, 1H), 3.42 (br s, 2H), 3.08 (br t, J=7.6 Hz, 2H), 2.71 (br t, J=7.6 Hz, 2H), 2.37 (br s, 3H), 2.27 (br s, 1H); Mass spectrum, calculated for $C_{15}H_{15}FN_2O$ m/z $[M+H]^+$=259.12, found $[M+H]^+$=259.0.

Ethereal HCl (2.0 M, 0.2 mL, 0.4 mmol) was added to a solution of compound 8 (34 mg, 0.13 mmol) in DCM (1 mL). After 30 min at rt, the mixture was concentrated in vacuo to dryness providing compound 8 dihydrochloride (42 mg, 96%) as a green solid: $^1$H NMR (400 MHz, $D_2O$, δ) 9.13 (d, J=8.4 hz, 1H), 9.06 (d, J=5.2 hz, 1H), 8.02 (dd, J=8.4 and 5.2 hz, 1H), 7.75 (d, $J_{HF}$=11.6 hz, 1H), 4.21 (d, J=2.4 hz, 2H), 3.64 (br s, 4H), 3.16 (t, J=2.4 hz, 1H), 3.10 (s, 3H).

Example 17

Stability of M30 and Derivatives in Aqueous Solution

M30 possesses unique neuropharmacologic properties, but the compound is also unstable in aqueous solution. This aqueous instability of M30 might be due to a phenolic hydroxyl-assisted solvolytic type loss of the N-methyl propargylamine moiety. This reaction is general-acid/general-base-catalyzed, suggesting that instability of M30 would be observed throughout the entire pH range. The veracity of this possibility is strongly supported by the outcome of aqueous stability studies of M30, compound 3, compound 4 and 8-methoxy-N-methyl-N-2-propyn-1-yl-5-quinolineethanamine, herein identified as [O-Methyl-Compound 3], predicted to be stable in aqueous solution, and also of a fourth M30 derivative, 5-(1-(methyl(prop-2-ynyl)amino)ethyl)quinolin-8-ol, which includes the addition of a methyl group at the benzyl methylene of M30, and which is predicted to be less stable than M30 itself. The result of the studies matched the predicted outcomes for each compound exactly (Table 1, below).

The aqueous stability of compounds 3, 4 and [O-Methyl-Compound 3], was confirmed and shown in Table 1. Using high pressure liquid chromatography (HPLC), the stability of each of the tested compounds was determined by following its respective chemical character over time in either phosphate buffered saline (PBS) and/or 0.85% saline solution (sodium chloride). In each case, 0.5 mM of the tested compound in PBS or saline solution was incubated at 25° C. or at 37° C. for 20 hours or, in some cases, up to two days (48 hours).

TABLE 1

Stability of M30 and derivatives in aqueous solution

| Experimental information | | | Amount of compound remaining (%) | | | |
|---|---|---|---|---|---|---|
| | Conditions | | | | | |
| | | Temp | Time (hours) | | | |
| Compound | Buffer | (° C.) | 0.5 | 2 | 20 | 48 |
| M30 | PBS | 25 | 76 | 57 | 28 | 15 |
| M30 | saline | 25 | 98 | 85 | 22 | nd |
| 5-(1-(methyl(prop-2-ynyl)amino)ethyl)-quinolin-8-ol | PBS | 25 | 0.0** | nd | nd | nd |
| Compound 3 | PBS+ | 25 | 100 | 100 | 100 | 100 |
| Compound 3 | saline+ | 25 | 100 | 100 | 100 | 100 |
| Compound 4 | PBS | 25 | 100 | 100 | 100 | 100 |
| Compound 4 | saline | 25 | 100 | 100 | 100 | 100 |
| [O-Methyl-Compound 3] | PBS | 25 | 100 | 100 | 100 | 100 |
| [O-Methyl-Compound 3] | saline | 37 | 100 | 100 | 100 | 100 |

*nd = not determined
**Decomposition of 5-(1-(methyl(prop-2-ynyl) amino)ethyl)quinolin-8-ol occurred immediately upon dissolution in PBS aspredicted by the working hypothesis
+Compound 3 was stable for up to 48 hours at 25° C. in both saline and PBS Compounds 3 and 4 and [O-Methyl-Compound 3] were highly stable chemically in PBS and saline solution for at least two full days at room temperature. [O-Methyl-Compound 3] was also stable in PBS at 37° C. for at least two days. M30 degraded in both PBS and saline solution. 5-(1-(methyl (prop-2-ynyl)amino)ethyl)quinolin-8-ol decomposed immediately in PBS solution at 25° C. Thus supporting the claim of increased stability over M30.

In addition, in a follow-up experiment the instability of M30, and the stability of compounds 3, 7 and 8 was also confirmed at 37° C. in PBS, Table 2, below.

TABLE 2

Stability of M30 and compounds 3, 7 and 8

| Com-pound | Time (hours) Amount of compound remaining (%) | | | | | | | |
|---|---|---|---|---|---|---|---|---|
| | 0.5 | 1 | 2 | 3 | 4 | 8 | 24 | 48 |
| M30 | 50.8 | 54.9 | 45.1 | nd | 24.3 | 14.4 | 4.26 | nd* |
| Compound 3 | nd | nd | nd | ≥100 | nd | 95.7 | ≥100 | 87.2 |
| Compound 7 | nd | nd | nd | 99.7 | nd | 97.7 | 94.1 | 100 |
| Compound 8 | nd | nd | nd | ≥100 | nd | 96.7 | ≥100 | ≥100 |

*nd = not determined

II Biological Section

Methods
(a) Metal Binding Properties

It is known that 8-quinolinol is a strong chelator for iron and has a higher selectivity for iron over copper. It is an important precondition for the antioxidative-type drugs because it is the excessive iron stores and iron-mediated generation of free radicals in the brain that are thought to be associated with neurodegenerative diseases. Therefore, only chelators with a higher selectivity for iron over copper are expected to chelate iron instead of copper and have potential neuroprotective effects. In order to discuss possible correlation between chelating properties of 8-quinolinol and its derivatives with their anti-oxidative ability, and the correlation between its derivative and the best established iron chelating drug, desferal, with antioxidative properties, a reliable measurement of the stability constants of the newly synthesized compounds is necessary. A spectrophotometric method is used for measurement of the iron-complexes stability constants of the compounds.

(b) Mitochondria Isolation

Male Sprague-Dawley rats (300-350 g) are decapitated and the brains are immediately isolated and cooled in ice-cold isotonic 10 mM Tris-HCl buffer (pH 7.5) containing 0.25 M sucrose, 2 mM EDTA and 2% bovine serum albumin free of fatty acids (isolation buffer), and homogenized with 50 mL glass-teflon homogenizer with a motor (Heidolf, Germany) at 200 rpm in a 1:10 (w/v) ratio isolation buffer. The homogenate is centrifuged at 1000 g for 10 min and the resultant supernatant then centrifuged at 10,000 g for 10 min. The pellet is washed with 10 mM Tris-HCl (pH 7.5), 0.25 M sucrose, and centrifuged again at 10,000 g for 10 min. This step is then repeated three more times. The pellet is resuspended in 10 mM Tris-HCl (pH 7.5), 0.25 M sucrose at a final concentration of 50-60 mg protein/mL. The samples are stored at −18° C. until use.

(c) Inhibition of Lipid Peroxidation

The radical scavenging/antioxidant properties of the compounds of formula I may be determined by the lipid peroxidation assay. This system has been used to measure the ability of antioxidants to protect biological lipid from free radical damage.

The ability of the compounds to inhibit lipid peroxidation as initiated by iron and ascorbate is examined in brain mitochondria preparation employing the malonaldehyde procedure (Gassen et al., 1996, *Eur. J. Pharmacol.* 308(2): 219-25; Ben-Shachar et al., 1991, *J Neurochem*, 56:1441-1444).

The experiments are carried out in triplicates. 7.5 µM of mitochondrial preparation (0.25 mg protein) are suspended in 750 µM of 25 mM Tris-HCl (pH 7.4) containing 25 pM ascorbic acid. Samples of the drugs to be tested are dissolved in water or ethanol and added to the suspension. The reaction is started by the addition of 2.5 or 5 µM $FeSO_4$ (from a 1 mM stock solution), and incubation for 2 h at room temperature. The reaction is stopped by addition of 750 µL of 20% (w/v) trichloroacetic acid (TCA). The samples are centrifuged at 12,000 g for 10 min. 500 µL of the supernatant is mixed with 500 µL of 0.5% (w/v) TBA and heated to 95° C. for 30 min. The absorption of TBA derivatives is measured photometrically at $\lambda$=532 nm Blank analysis is based on emission of the mitochondria, or of $FeSO_4$, or alternatively, addition of the drugs after incubation.

(d) Neuroprotective Effects

Neuroprotective effects of the iron chelators are determined both in vivo and in vitro systems.

For in vitro experiments, rat pheochromocytoma type 12 (PC12) cells and human neuroblastoma SH-SY5Y cells are used to examine the neuroprotective action of the chelators in response to iron and beta-amyloid toxicity. Cell viability is tested in 2,5-diphenyltetrazolium bromide (MTT) and lactate dehydrogenase(LDH) tests as well as measuring dopamine and tyrosine hydroxylase by HPLC and release of alpha-amyloid (soluble) by Western, since these cells are used as models of dopamine and cholinergic neurons.

The protection in vivo is tested in 1-methyl-4-phenyl-1,2,3,6-tetrahydropyridine (MPTP) animal model of Parkinson's disease (PD), a very viable and well-established model of neurodegeneration, by measuring striatal dopamine and tyrosine hydroxylase, the markers of dopamine neurons.

(e) PC12 Cell Culture.

Rat PC12 cells, originated from rat pheochromocytoma, are grown at 37° C., in a humid 5% $CO_2$, 95% air environment, in a growth medium containing Dulbecco's modified Eagle's Medium (DMEM, GIBCO, BRL) supplemented with glucose (1 mg/mL), 5% fetal calf serum, 10% horse serum, and 1% of a mixture of streptomycin/penicillin. On confluence, the culture is removed and the cells are detached by vigorous washing, centrifuged at 200 g for 5 min and resuspended in DMEM with full serum content. $0.5 \times 10^4$ cells/well are placed in microtiter plates (96 wells) precoated with collagen.

(f) MTT Tests for Cell Viability.

Twenty-four hours after attachment of the PC12 cells as described in (f), the medium is replaced with DMEM containing 0.1% bovine serum albumin (BSA). The test compounds are added to the cells after 1 h of incubation. After 24 h incubation, the cells are subjected to MTT test as previously described (Gassen et al., 1998, *Movement Disorders* 13:242-248). The absorption is determined in a Perkin-Elmer Dual Wavelength Eliza-Reader at $\lambda=570/650$ nm after automatic subtraction of background readings. The results are expressed as percentage of the untreated control.

(g) Screening Assays:

Step 1—Oral Availability:

Among the screening assays oral availability of each compound of formula I, for example, is completed using a rapid rodent oral estimation. For each test article and possibly certain metabolites, a simple extraction and LC-MS/MS (API4000) analytical method is developed following a brief test evaluating plasma stability. Test articles are prepared in either: water, saline solution, TWEEN, PEG or a similar common vehicle. Three healthy rats of either gender are dosed at predetermined levels (likely in a range of 10-20 mg/kg) at one time via oral gavage. Blood is then collected at four time points (1, 2, 4 and 8 hours) or more as appropriate. Plasma samples (12 per test article) are prepared and analyzed via LC-MS/MS. PK parameters are estimated using WinNonlin software (Pharsight Corp.)

Step 2—PK Parameters:

If a compound of formula I (or active metabolite) proved to be orally available (at least 15% absorption), PK parameters are estimated in rats for selected compounds of formula I (and active metabolites), using LC-MS/MS methods for each derivative and for M30 itself (as above). PK studies use six cannulated rats of either gender per test article, three of which are dosed only once intravenously and three via oral gavage. Following dosing blood is collected at seven timepoints for each rat (0.5, 1, 2, 4, 6, 8, and 12 hours) and nine timepoints for each rat treated by the intravenous route (5, 15 and 30 minutes and 1, 2, 4, 6, 8, and 12 hours). Plasma is prepared and analysis is conducted as in the oral availability screen. PK parameters ($C_{max}$, $T_{max}$, $V_d$, AUC and bioavailability) are determined for individual animals using non-compartmental analysis using WinNonlin software (Pharsight Corp).

(h) Topical Photoprotection

In order to determine the level of topical photoprotection provided by the iron chelators of the invention, guinea pigs are treated topically with the test compound, and are then exposed to varying doses of UV radiation to determine the sun protection factor (SPF). Hairless mice are treated topically with the test compound and then subjected to long-term exposure to a suberythemal dose of UV radiation. The mice are evaluated for skin wrinkling and skin tumors.

In another experiment, guinea pigs are treated topically with the test compound, sunscreen, and a combination of the two and are then exposed to varying doses of UV radiation to determine the sun protection factor (SPF). Hairless mice are treated topically with the test compound, sunscreen, and a combination of the two and then subjected to long-term exposure to a suberythemal dose of UV radiation. The mice are evaluated for skin wrinkling and skin tumors.

Example 18

Determination of MAO Inhibitory Activity In Vitro

Preparation of Brain MAO

Rats are decapitated and the brains quickly taken into a weighted ice-cold sucrose buffer (0.32 M) and their weights determined. All subsequent procedures are performed at 0° C. The brains are homogenized in 0.32 M sucrose (one part tissue to 20 parts sucrose) in a Teflon glass homogenizer followed by the addition of sucrose buffer to a final concentration of 10% homogenate. The homogenates are centrifuged at 600 g for 15 min. The supernatant fractions are taken out and centrifuged at 4500 g for 30 min, the pellet diluted in 0.32 M sucrose buffer and kept frozen for later assaying of MAO. Protein concentration is determined with Bradford reagent at $\lambda=595$ nm, using BSA as a standard.

Inhibition of MAO-A and MAO-B by the Iron Chelators

MAO-A and MAO-B activities are determined in rat brain homogenate in vitro following incubation with varying concentrations of the test compounds.

The in vitro inhibitory activity of the compounds is tested against rat brain MAO-B. The test compounds are added to buffer containing $10^{-7}$ M clorgylin and are incubated with the tissue homogenate for 30 or 60 min at 37° C. before addition of $^{14}$C-PEA.

The activity of MAO-A and MAO-B was determined by the adapted method of Tipton & Youdim (Tipton K F, O'Sullivan J, Youdim M B, 1983, *Encyclopedia of Neuroscience*, 2004, G. Adelman and B. H. Smith, Elsevier). The test compound was added to a suitable dilution of the enzyme preparation (70 µg protein for MAO-B and 150 µg MAO-A assay) in 0.1 M phosphate buffer (pH 7.4). The mixture was incubated together with 0.05 M deprenyl/selegiline, a specific inhibitor of MAO-B (for determination of MAO-A) or 0.05 M clorgylin, a specific inhibitor of MAO-A (for determination of MAO-B). Incubation was carried for 0.5 or 1 h at 37° C. before addition of $^{14}$C-5-hydroxytryptamine binoxalate (5-HT) (100 or 400 µM) for determination of MAO-A, or $^{14}$C-phenylethylamine ($^{14}$C-PEA) 100 or 400 µM for determination of MAO-B, and incubation continued for 30 min or 20 min, respectively. The reaction was stopped with 2 M ice-cold citric acid, and the metabolites were extracted and determined by liquid-scintillation counting in cpm units.

Example 19

Inhibition of MAO-A and MAO-B by O-Methyl-M30

The MAO-A and MAO-B inhibitory capacity of O-methyl-M30 was compared with that of rasagiline, a known potent and specific inhibitor of MAO-B. Rasagiline (Azilect®; Agilect®) is an approved drug used for treatment of Parkinson's disease. In a recent large clinical study of Parkinson's disease patients, rasagiline was found to have disease modifying potential. Samples of O-methyl-M30 and the control rasagiline were incubated with rat brain extracts. Striatal monoamine oxidase (MAO) activity was determined using $^{14}$C-PEA as a substrate for MAO-B as previously described in Grunblatt, et al. (2001, *J. Neurochem.*, 77:146-56). Specifically, MAO-A and MAO-B activity were estimated according to Tipton and Youdim (2004, *Encyclopedia of Neuroscience*, G. Adelman and B. H. Smith, Elsevier), with the following modifications: triplicates of 150 or 70 μg protein homogenate of rat brain regions, liver and small intestine were incubated with $^{14}$C-5HT (100 μM), for 30 min, (final concentration 100 μM), as a substrate for MAO-A, or $^{14}$C-phenylethylamine for 20 min, (final concentration 10 μM), as a substrate for MAO-B, respectively. For determination of MAO-A or MAO-B, brain homogenates were preincubated with 75 nM 1-deprenyl or 75 nM clorgyline, respectively, for one hour at 37° C. prior to the addition of the substrates. The reaction was stopped with 2 M ice-cold citric acid, and the metabolites were extracted with ethyl acetate and levels of radioactivity were determined by liquid-scintillation counting in CPM units. All assays were performed at least in duplicate and outcome was expressed as a mean±SEM. Data were analyzed by a Student's t test. Variations were considered statistically significant at a p value of 0.05. The results are presented in Table 3.

TABLE 3

Inhibition of MAO-A and MAO-B by O-Methyl-M30

MAO-A Inhibition

| Compound | Concentration (mM) | Inhibition of brain MAO-A (%) |
|---|---|---|
| Rasagiline | 0.001 | 47.4 |
| | 1.0 | 99.8 |
| O-Methyl-M30 | 0.01 | 98.5 |
| | 0.1 | 99.7 |

MAO-B Inhibition

| Compound | Concentration (mM) | Inhibition of brain MAO-B (%) |
|---|---|---|
| Rasagiline | 0.001 | 99.5 |
| | 1.0 | 99.7 |
| O-Methyl-M30 | 0.01 | 87.8 |
| | 0.1 | 97.3 |

It is evident that O-methyl M30 inhibits both brain MAO-A and MAO-B at apparently similar levels. This inhibitory activity is consistent with the activity of the parent M30. In contrast rasagiline inhibits MAO-B very strongly but MAO-A more poorly as expected.

Example 20

Inhibition of MAO-A and MAO-B by O-Methyl-M30, Compounds 3 and 4

Figure 2:
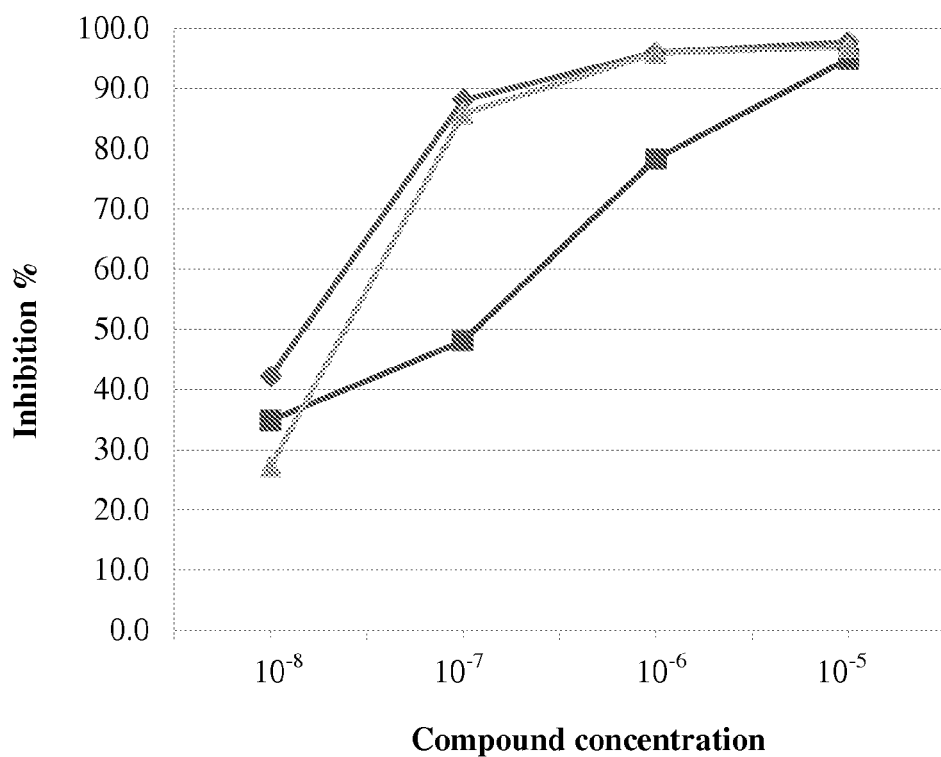
FIG. 2 shows inhibition of rat brain MAO-B by the compounds 3 (diamonds), 4 (squares) and M30 (triangles) in vitro.

MAO-A and MAO-B activity was measured using radioactive substrates. The substrate for MAO-A was 5 HT and for MAO-B was PEA. When measuring the activity of MAO-A, the MAO-B activity was inhibited with deprenyl and when measuring the activity of MAO-B the activity of MAO-A was inhibited with clorgylin. Blank samples were produced using TCP to inhibit both of the enzymes. The metabolites were extracted to toluene and read in a β-counter. The results are expressed in relative activity and normalized to the amount of protein in the tissue. FIGS. 1 and 2 show MAO-A/MAO-B activity of compounds 3, 4 and of O-Methyl-M30 at various concentrations ($10^{-5}$-$10^{-8}$). As presented in FIGS. 1 and 2, it can be seen that compounds 3, 4 and O-Methyl-M30 were all potent inhibitors of MAO-A and MAO-B extracted from rat brain, compound 3 clearly the most potent inhibitor of the three compounds.

It can be estimated from the data in FIG. 1 (assuming a log scale) that the MAO-A $IC_{50}$ for compound 3 is about 70-90 nM or better, for compound 4 is about 200 nM, and for O-Methyl-M30 is about 250-300 nM. For comparison, the MAO-A $IC_{50}$ of M30 is 37 nM and that of rasagiline (Azilect®) is 410 nM.

The $IC_{50}$ data for the compounds 3, 4, O-Methyl-M30, M30 and rasagiline are summarized in Table 4.

TABLE 4

In Vitro MAO Inhibition Data

| Compound | MAO-A $IC_{50}$ (nM) | MAO-B $IC_{50}$ (nM) |
|---|---|---|
| Rasagiline | 410 | 4 |
| M30 | 37 | 57 |
| Compound 3 | 70-90 | 10-30 |
| Compound 4 | 200 | 100 |
| O-Methyl-M30 | 250-300 | 20-40 |

Example 21

Inhibition In Vivo of MAO-A and MAO-B by Compound 3

Figure 3:
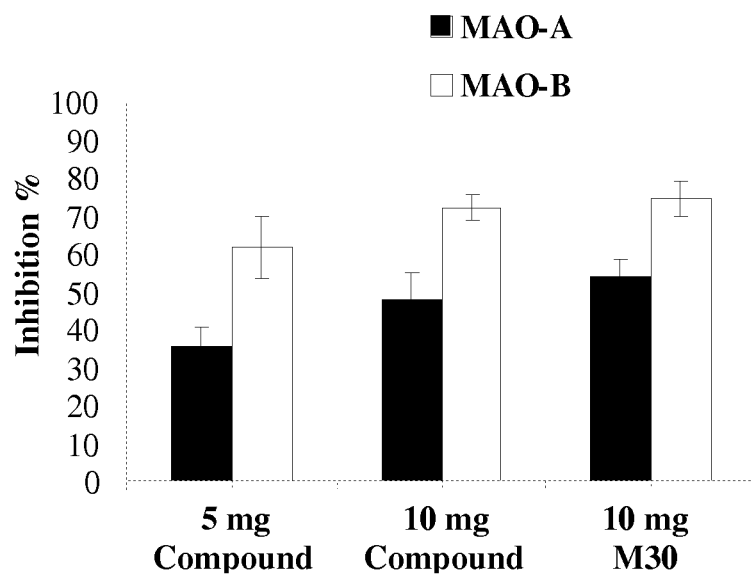
FIG. 3 shows inhibition of MAO-A and MAO-B levels in striatum of brains of mice receiving a single intraperitoneal injection of either compound 3 or M30.
Figure 4:
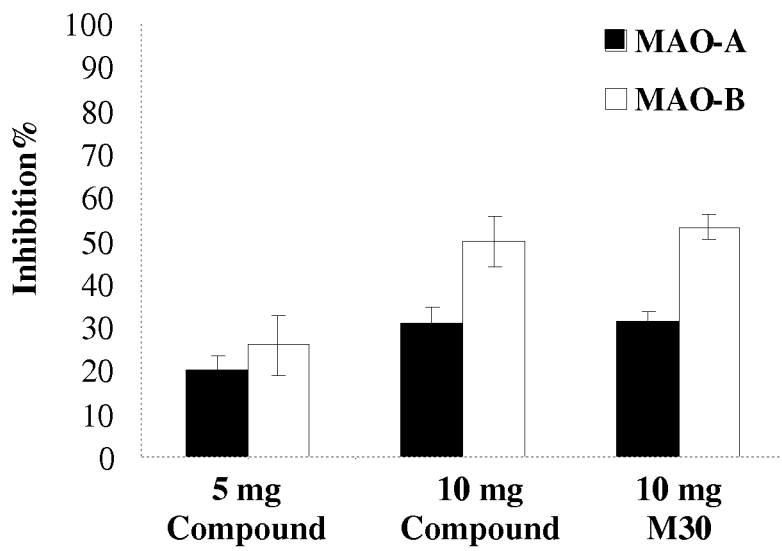
FIG. 4 shows inhibition of MAO-A and MAO-B in intestine of mice receiving a single intraperitoneal injection of either compound 3 or M30.

For the MAO-inhibition study, mice (6 mice in each group) were injected intraperitoneally (i.p.) with compound 3 at the dosage of 5 or 10 mg/kg; or with M30 at the dosage of 10 mg/kg. Control mice received saline (0.1 mL) i.p. One hour later the mice were killed by cervical dislocation, while striatum and small intestine were removed rapidly and frozen in liquid nitrogen for further analysis. FIGS. 3 and 4 show MAO-A/MAO-B in vivo activity of compound 3 compared to the activity of M30. FIG. 3 presents an MAO inhibition in striatum, and FIG. 4 presents an MAO inhibition in intestine. The percent inhibition was computed based on comparison to control animals.

It can be seen that after a single injection of compound 3, both MAO-A and MAO-B in the brains of treated animals were inhibited in a dose responsive fashion, indicating that the compound was able to penetrate brain tissue and inhibit the target enzymes. In addition, the levels of inhibition at 10 mg/kg were nearly identical to those seen when M30 was administered to the animals. For reference, it has been reported that significant improvement in various biochemical and behavioral parameters associated with neurotoxic challenges could be seen in animals given doses of M30 as low as 1 mg/kg orally or intraperitoneally. Moreover, in addition to the striatum, M30 has been reported to inhibit MAO isozyme levels in the hippocampus and cortex of the brain. The ability to inhibit both MAO isozymes is an important consideration because this property provides for increased levels of dopamine, serotonin and other neurotransmitters.

The intestinal inhibition of the MAO isozymes was also measured using both compound 3 and M30 (FIG. 4). Reduced inhibition in the intestinal tissue versus striatal tissue was observed with both compound 3 and M30. Moreover, the compound 3 results once again matched the M30 results at the 10 mg/kg dose. It can be concluded from these analyses that compound 3 is taken up by the brain, consistent also with the findings for M30 and O-Methyl-M30, and that in the brain it can inhibit both MAO-A and MAO-B at levels sufficient to be clinically relevant.

Example 22

Plasma Stability of Compound 3 In Vitro

The stability of the compound 3 was evaluated in human blood plasma. Human plasma was purchased from a commercial source (Bioreclamation, Inc., East Meadow, N.Y.). The plasma was prepared from blood collected using sodium fluoride/potassium oxalate as the anticoagulant. The plasma was stored at −20° C. prior to use. The plasma, once thawed for use, was centrifuged at ~4000 rpm for five minutes and transferred to a new tube to remove any precipitate. The pH of the plasma was adjusted to 7.4. Compound 3 was added to plasma samples to achieve a final concentration of 10 μM and distributed into the required number of low retention tubes (triplicate tubes for each timepoint) for incubation at ~37° C. in a water bath. Incubations were terminated at 0, 1, and 6 hours by the addition of three volumes of cold acetonitrile. The supernate after centrifugation was subjected to LC-MS/MS analysis. Stability of the test article was assessed by comparison of the peak area at one and six hours to that at time zero. Results are presented in Table 5. According to Table 5, six hours after administration compound 3 was still present in the plasma (93%), suggesting that this compound is stable in the plasma.

TABLE 5

Stability of compound 3 in Human Blood Plasma

| Time (hour) | Amount of compound 3* |
|---|---|
| 0 | 100% |
| 1 | 86% |
| 6 | 93% |

*Values are an average of triplicates

Example 23

In Vitro Cytoxicity of Compound 3

The acute in vitro cytotoxicity of each of several selected compounds of formula I is determined. The cytotoxicities are compared to cytotoxicities of related compounds, for example, DFO.

The cytotoxicity of compound 3 was assessed in vitro using two standard cell lines, HepG2, derived from a human hepatocellular carcinoma, and SH-SY5Y, derived from a human neuroblastoma, both in the presence and absence of excess iron.

HepG2 cells were maintained at ~5% $CO_2$, 37° C., and 95% relative humidity in minimal essential media (MEM) supplemented with 10% fetal bovine serum plus 0.1 mM non-essential amino acids, 2 mM L-glutamine, and penicillin/streptomycin. SH-SY5Y cells were maintained at ~5% $CO_2$, 37° C., and 95% relative humidity in a mixture of minimal essential media (MEM) and F12 K media (1:1, v:v) supplemented with 10% fetal bovine serum plus 0.1 mM non-essential amino acids, 2 mM L-glutamine, and penicillin/streptomycin. The cells were subcultured every two to three days and plated in tissue culture treated opaque white 96-well plates at a density of $1\times10^4$ cells/well and incubated at ~5% $CO_2$, 37° C., and 95% relative humidity overnight prior to initiation of the assay.

A series of DMSO stocks of the test article at 100× of the final concentration were diluted 1:100 with fresh culture media (final DMSO concentration was 1%). The media from the plated cells was removed and replaced with 100 μL of media containing test article or tamoxifen with final concentrations ranging between 0.01 to 1000 μM in triplicate. Wells containing no cells were used as background controls. Tamoxifen was used as a known positive control and DMSO alone was used as a vehicle control. The cells were incubated for four hours at ~5% $CO_2$, 37° C., and 95% relative humidity.

Cell viability was determined using a commercially available kit to determine ATP levels by luminescence. Briefly, the buffer and lyophilized substrate from the kit were equilibrated to room temperature. The buffer was used to reconstitute the substrate just prior to addition to the wells of the cell plate (100 μL per well). The plate was placed into the Tecan Infinite M200 plate reader, agitated for 10 minutes followed by a 10 minute wait period, then read using an integration time of 0.5 seconds with no attenuation.

The mean baseline controls (wells with no cells) were subtracted from the total luminescence to give the net luminescence. The mean luminescence from the test article treated cells was compared to that treated by DMSO only. The $LC_{50}$ was defined as the concentration of compound 3 that leads to a 50% decrease in luminescence signal compared to the vehicle control-treated cells.

The potential of compound 3 to be toxic in the presence of free iron was also tested. The iron complexation method was based on the method of Leanderson and Tagesson (*Carcinogenesis,* 17, 545-550, 1996) with some modifications. Iron (III) was prepared from ferric ammonium citrate (Sigma, F5879) at 80 mM in sterile distilled water. Compound 3 was prepared at a 200 mM concentration in DMSO. Before each experiment, the freshly prepared iron (III) solution was diluted to 0.4 mM in PBS II (PBS containing 0.90 mM $Ca^{2+}$ and 0.49 mM $Mg^{2+}$). Compound 3 stock solutions were diluted to 2, 0.2, and 0.02 mM with PBS II. Equal volumes of the 0.4 mM iron (III) solution and compound 3 solutions were added together to prepare iron/test article complex solutions containing 1, 0.1, and 0.01 mM compound 3 and 0.2 mM iron (III). The compound 3 DMSO stock solution was diluted in PBS II at 1, 0.1, or 0.01 mM and used as compound 3 control without iron. An equal volume of the 0.4 mM iron (III) solution was diluted in PBS II to prepare a control containing only iron.

The medium was removed from the plated cells (both cell lines) and replaced with fresh medium (90 μL). Iron/compound 3 complex or compound 3 in PBS II without iron was added to cells in triplicate (10 μL) to final compound 3 concentrations of 100, 10, and 1 μM and an iron (III) concentration of 20 μM. Wells containing no cells were used as the background control. PBS II was run as vehicle control. Iron only was run at a final concentration of 20 μM. The cells were incubated for four hours at 5% $CO_2$, 37° C., and 95% relative humidity.

Cell viability was determined as described above and cytotoxicity was compared between treatments with and without iron complexation.

Figure 5A:
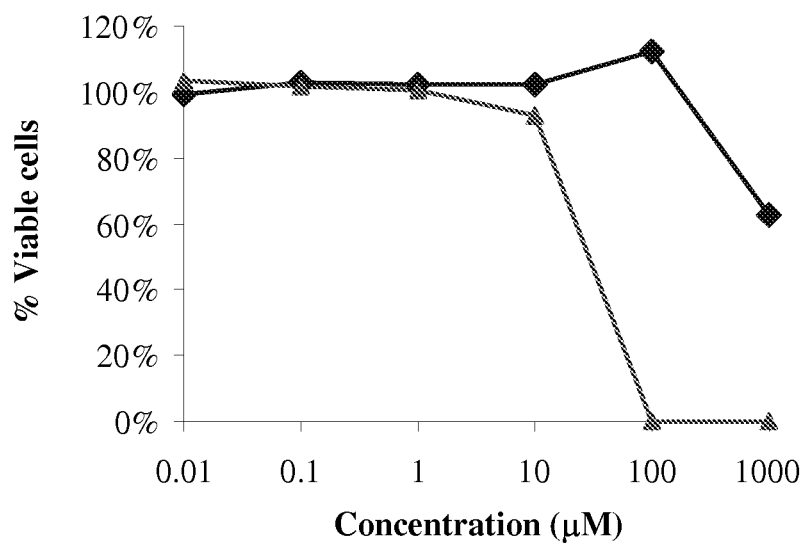
FIGS. 5A-5B are graphs showing the cytotoxicity of compound 3 (diamonds) and of Tamoxifen (triangles) for HepG2 cells.
Figure 5B:
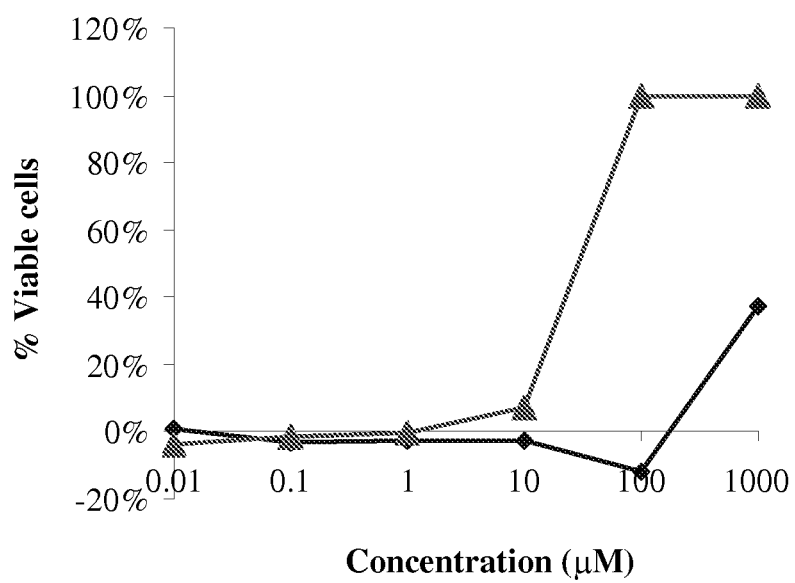
Figure 6A:
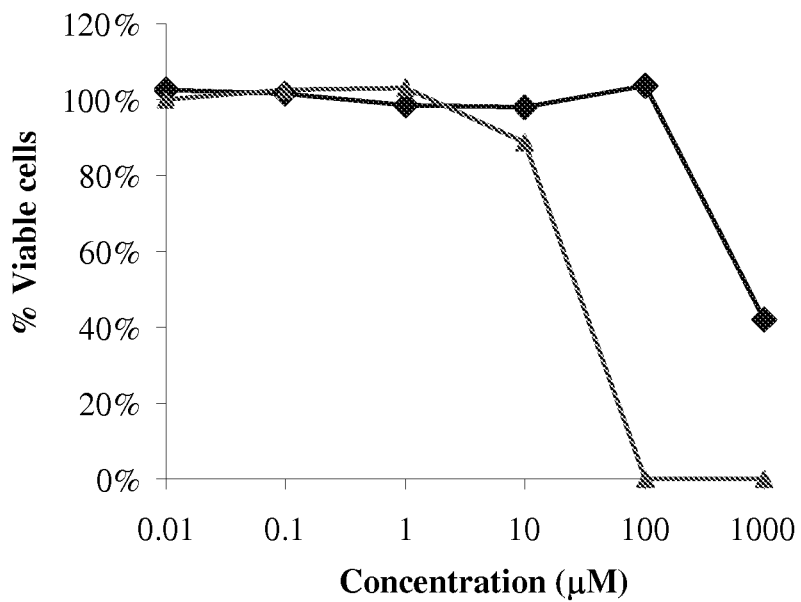
FIGS. 6A-6B are graphs showing the cytotoxicity of compound 3 (diamonds) and of Tamoxifen (triangles) for SHSY-5Y cells.
Figure 6B:
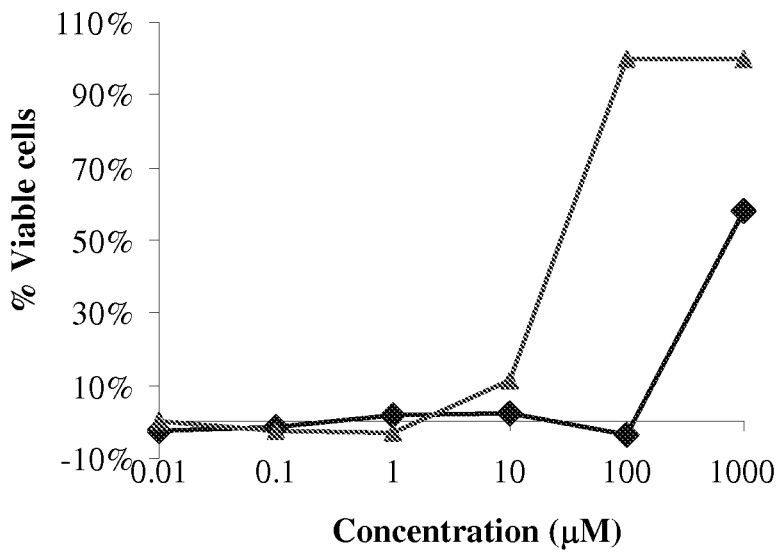

FIGS. 5B and 6B disclose the cytotoxic properties of compound 3, for HepG2 and SH-SY5Y. The compound 3 $LC_{50}$ s for SHSY-5Y and HepG2 cells were 865 μM and greater than 1,000 μM, respectively, compared to the tamoxifen control with an $LC_{50}$ for each cell line of about 50 μM.

The cytotoxicity of the combination of compound 3 and free iron in HepG2 and SHSY-5Y cells was also evaluated using an exogenous iron concentration of 20 μM. For reference, it has been reported that free iron or chelatable iron concentrations in the cytosol or mitochondria of various cell types range from 4-12 μM. In the experiment, 20 μM exogenous iron was not cytotoxic, nor was compound 3 alone.

Figure 7:
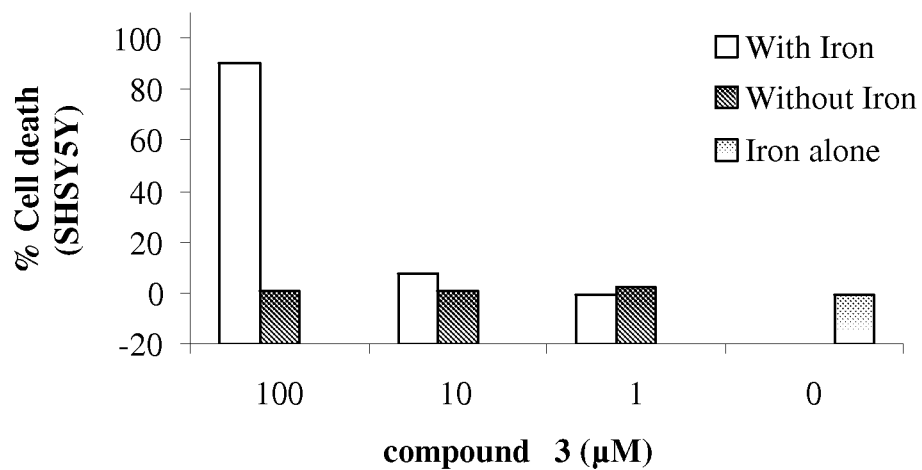
FIG. 7 shows cytotoxicity of compound 3 for SHSY-5Y cells in the presence or absence of 20 μM exogenous iron.
Figure 8:
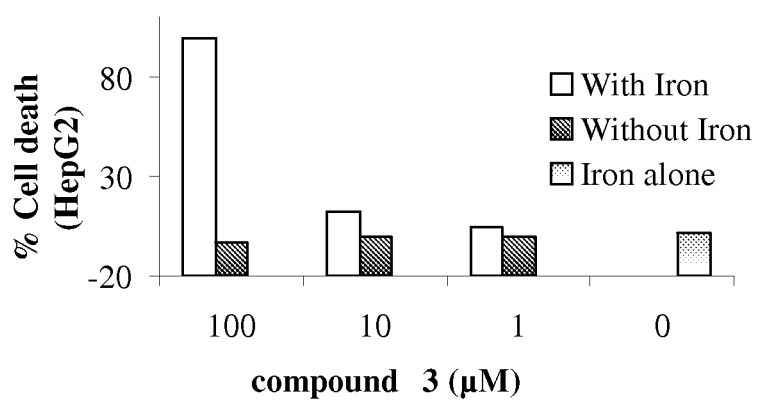
FIG. 8 shows cytotoxicity of compound 3 for HepG2 cells in the presence or absence of 20 μM exogenous iron.

Only at very high concentrations of compound 3 (100 μM) in the presence of iron was substantial cytotoxicity observed (see FIGS. 7 and 8). In the presence of exogenous iron at a compound 3 concentration of 1 μM, the fraction of dead HepG2cells was only 4.8% and 100% of the SHSY-5Y cells were alive.

In conclusion compound 3 is not cytotoxic at concentrations relevant for treatment. Moreover, the outcomes of the cytotoxicity experiments compare very favorably with those conducted in the past with M30. Although the methods were not identical it is nonetheless instructive to note that $LC_{50}$ levels for compound 3 alone were very similar to those for M30 and in the presence of iron compound 3 results were better than those for M30 (Tables 6 and 7).

TABLE 6

Comparison of M30 and compound 3 Cytotoxicity

| Compound | Cell Line and $LC_{50}$ (μM) | | |
|---|---|---|---|
|  | A549 | HepG2 | SHSY-5Y |
| Compound 3 | ND* | >1,000. | 885. |
| M30 | >1,000. | 842. | >1,000. |

*ND = not determined

TABLE 7

M30 and compound 3 cytotoxicity in the presence and absence of exogenous Iron

| Com-pound | With Iron | | | Without iron | | | Iron Alone | Vehicle |
|---|---|---|---|---|---|---|---|---|
|  | 100 | 10 | 1 | 100 | 10 | 1 | 0 | 0 |
| compound 3 (μM) | | | | | | | | |
| HepG2 cell death (%) | 99.5 | 11.9 | 4.8 | -3.6 | -0.7 | -0.1 | 1.6 | 0.0 |
| SHSY-5Y cell death (%) | 90.3 | 7.6 | -1.0 | 0.4 | 0.8 | 2.1 | -1.0 | 0.0 |
| M30 (μM) | | | | | | | | |
| SHSY-5Y cell death (%) | 38.5 | 78.6 | 0.69 | 19. | 1.0 | -2. | ND* | 0 |

*ND = not determined

REFERENCES

Andrews F. J., Morris C. J., Kondratowicz G., Blake, D. R., (1987) "Effect of iron chelation on inflammatory joint disease", Ann. Rheum. Dis., 46(4):327-33.

Ben-Shachar, D., Eshel, G., Finberg, J. P. and Youdim, M. B., (1991) "The iron chelator desferrioxamine (Desferal) retards 6-hydroxydopamine-induced degeneration of nigrostriatal dopamine neurons.", J. Neurochem., 56:1441-1444.

Bissett, D. L. and McBride, J. F., (1996) "Synergistic topical photoprotection by a combination of the iron chelator 2-furildioxime and sunscreen", J. Am. Acad. Dermatol. 35(4): 546-9.

Breuer, W., Epsztejn, S., Millgram, P., and Cabantchik, I. Z., (1995) "Transport of iron and other transition metals into cells as revealed by a fluorescent probe", Am. J. Physiol., 268(6 Pt 1):C1354-61.

Buss, J. L., Torti, F. M., and Torti, S. V., (2003) "The role of iron chelation in cancer therapy", Curr. Med. Chem., 10(12):1021-34.

Butterfield, D. A., Howard, B. J., and LaFontaine, M. A., (2001) "Brain oxidative stress in animal models of accelerated aging and the age-related neurodegenerative disorders, Alzheimer's disease and Huntington's disease", Curr. Med. Chem., 8(7):815-28.

Crivori, P., Cruciani, G., Carrupt, P. A., and Testa, B., (2000) "Predicting Blood-Brain Barrier Permeation from Three-Dimensional Molecular Structure", J. Med. Chem., 43:2204-2216.

Cuajungco, M. P., Faget, K. Y., Huang, X., Tanzi, R. E., and Bush, A. I., (2000) "Metal chelation as a potential therapy for Alzheimer's disease", Ann. N.Y. Acad. Sci., 920:292-304.

Flaherty, J. T. and Zweier, J. L., (1991) "Role of oxygen radicals in myocardial reperfusion injury: experimental and clinical evidence", Klin. Wochenschr., 69(21-23): 1061-5.

Gassen, M. and Youdim, M. B., (1999) "Free radical scavengers: chemical concepts and clinical relevance", J. Neural. Transm. Suppl., 56:193-210.

Gassen, M., Gross, A. and Youdim, M. B., (1998) "Apomorphine enantiomers protect cultured pheochromocytoma (PC12) cells from oxidative stress induced by $H_2O_2$ and 6-hydroxydopamine.", Movement Disorders, 13:242-248.

Gassen, M. and Youdim, M. B., (1997) "The potential role of iron chelators in the treatment of Parkinson's disease and related neurological disorders.", Pharmacol. Toxicol., 80(4): 159-66.

Gassen, M., Glinka, Y., Pinchasi, B., and Youdim, M. B., (1996) "Apomorphine is a highly potent free radical scavenger in rat brain mitochondrial fraction", Eur. J. Pharmacol., 308(2):219-25.

Gozes, I., Pert, O., Giladi, E., Davidson, A., Ashur-Fabian, O., Rubinraut, S., and Fridkin, M., (1999) "Mapping the active site in vasoactive intestinal peptide to a core of four amino acids: neuroprotective drug design.", Proc. Natl. Acad. Sci. U.S.A., 96(7):4143-8.

Grunblatt, E, Silvia Mandel, Gila Maor, and Moussa B. H. Youdim, (2001), "Effects of R- and S-apomorphine on MPTP-induced nigro-striatal dopamine neuronal loss.", J. Neurochemistry, 77:146-56.

Hahn, P., Milam, A. H., and Dunaief, J. L., (2003) "Maculas affected by age-related macular degeneration contain increased chelatable iron in the retinal pigment epithelium and Bruch's membrane", Arch. Ophthalmol., 2003, 121 (8): 1099-105.

Hershko, C., (1994) "Control of disease by selective iron depletion: a novel therapeutic strategy utilizing iron chelators", Eur. J. Biochem., 270(8):1689.

Hershko, C, Pinson, A, and Link, G., (1996) "Prevention of anthracycline cardiotoxicity by iron chelation", Acta Haematol., 95(1):87-92.

Hewitt, S. D., Hider, R. C., Sarpong, P., Morris, C. J., and Blake, D. R., (1989) "Investigation of the anti-inflammatory properties of hydroxypyridinones", Annals of Rheum. Diseases, 48:382-388.

Kitazawa, M. and Iwasaki, K., (1999) "Reduction of ultraviolet light-induced oxidative stress by amino acid-based iron chelators", Biochim. Biophys. Acta., 27; 1473(2-3): 400-8.

Kontoghiorghes, G. J., (2001) "Clinical use, therapeutic aspects and future potential of deferiprone in thalassaemia and other conditions of iron and other metal toxicity", Drugs of Today, Vol. 37, pages 23-35.

Ostrakhovitch, E. A. and Afanas'ev, I. B., (2001) "Oxidative stress in rheumatoid arthritis leukocytes: suppression by rutin and other antioxidants and chelators", *Biochem. Pharmacol.,* 62(6):743-6.

Podda, M, and Grundmann-Kollmann, M., (2001) "Low molecular weight antioxidants and their role in skin ageing", *Clin. Exp. Dermatol.,* 26(7):578-82.

Polla, A. S., Polla, L. L., Polla, B. S., (2003) "Iron as the malignant spirit in successful ageing", *Ageing Res. Rev.,* 2(1):25-37.

Roza, A. M., Slakey, D. P., Pieper, G. M., Van Ye, T. M., Moore-Hilton, G, Komorowski, R. A., Johnson, C. P., Hedlund, B. E., and Adams, M. B., (1994) "Hydroxyethyl starch deferoxamine, a novel iron chelator, delays diabetes in BB rats", *J. Lab. Clin. Med.,* 123(4):556-60.

Sawahara, H, Goto, S, and Kinoshita, N., (1991) "Double fluorescent labeling method used for a study on liposomes", *Chem. Pharm. Bull.* (Tokyo), 39(1):227-9.

Sayre, L. M., Perry, G, Atwood, C. S, and Smith, M. A., (2000) "The role of metals in neurodegenerative diseases", *Cell. Mol. Biol.,* 46:731-741.

Sepulchre, A., Vass, G., and Gero, S., *Tet. Letters,* 1973, 3619.

Skjaeret, T., and Benneche, T., *ARKIVOC,* 2001, 16-25.

Song, X., Balvinder, S., Lorenzi, P., Drach, J., Townsend, L., and Amidon, G., *J. Med. Chem.,* (2005), 48, 1274-1277.

Tipton, K. F., O'Sullivan, J., and Youdim, M. B., *Encyclopedia of Neuroscience,* (2004), G. Adelman and B. H. Smith, Elsevier.

van Asbeck, B. S., Georgiou, N. A., van der Bruggen, T., Oudshoorn, M., Nottet, H. S., and Marx, J. J., (2001) "Anti-HIV effect of iron chelators: different mechanisms involved", *J. Clin. Virol.,* 20(3): 141-7.

Vile, G. F. and Tyrrell, R. M., (1995) "UVA radiation-induced oxidative damage to lipids and proteins in vitro and in human skin fibroblasts is dependent on iron and singlet oxygen", *Free Radic. Biol. Med.,* 18(4):721-30.

Yogev-Falach, M., Amit, T., Bar-Am, O., and Youdim, M. B., (2003) "The importance of propargylamine moiety in the anti-Parkinson drug rasagiline and its derivatives for MAPK-dependent amyloid precursor protein processing.", *FASEB J.,* 2003 Oct. 2 [Epub ahead of print].

The invention claimed is:

1. A compound of the formula I:

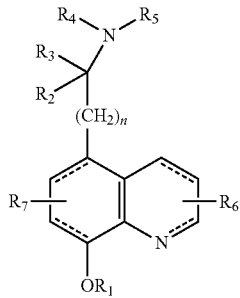

wherein $R_1$ is selected from the group consisting of:

(i) H;

(ii) $C_1$-$C_8$ alkyl substituted by one or more radicals selected from the group consisting of hydroxy, $C_1$-$C_8$ alkoxy, cyano, carboxy, aminocarbonyl, $C_1$-$C_8$ (alkyl)aminocarbonyl, di($C_1$-$C_8$)alkylaminocarbonyl, $C_1$-$C_8$ (alkoxy)carbonyl, and $C_1$-$C_8$ (alkyl)carbonyloxy;

(iii) —$COR_8$, wherein $R_8$ is $C_1$-$C_8$ alkyl, $C_2$-$C_8$ alkenyl, $C_2$-$C_8$ alkynyl, $C_3$-$C_8$ cycloalkyl, aryl, or heteroaryl, wherein said alkyl, alkenyl, alkynyl, aryl, or heteroaryl group is optionally substituted by one or more of the following groups: halogen atoms, $C_1$-$C_8$ alkyl, hydroxy, amino, $C_1$-$C_8$ alkylamino, di($C_1$-$C_8$)alkylamino, mercapto, $C_1$-$C_8$ alkylthio, cyano, $C_1$-$C_8$ alkoxy, carboxy, $C_1$-$C_8$ (alkoxy)carbonyl, $C_1$-$C_8$ (alkyl)carbonyloxy, $C_1$-$C_8$ (alkyl)sulfonyl, $C_1$-$C_8$ (alkyl)carbonylamino, aminocarbonyl, $C_1$-$C_8$ (alkyl)aminocarbonyl, or di($C_1$-$C_8$)alkylaminocarbonyl, or a $C_1$-$C_5$ alkyl group is substituted by an amino group at the α-position to the CO group and may be further substituted by a group selected from the group consisting of hydroxy, methylthio, mercapto, phenyl, hydroxyphenyl, indolyl, aminocarbonyl, carboxy, amino, guanidino, and imidazolyl;

(iv) -$COOR_9$, wherein $R_9$ is $C_1$-$C_8$ alkyl optionally substituted by halogen, $C_1$-$C_8$ alkoxy, phenyl optionally substituted by nitro, hydroxy, carboxy, or $C_3$-$C_6$ cycloalkyl; $C_2$-$C_4$ alkenyl; $C_2$-$C_4$ alkynyl; $C_5$-$C_7$ cycloalkyl; or phenyl optionally substituted by halogen, amino, nitro, $C_1$-$C_8$ alkyl, $C_1$-$C_8$ (alkoxy)carbonyl, or $C_1$-$C_8$ alkoxy;

(v) —$CH_2$—O—CO—$R_{10}$, or —$CH(CH_3)$—O—CO—$R_{10}$, wherein $R_{10}$ is $C_1$-$C_8$ alkyl optionally substituted by halogen or $C_1$-$C_8$ alkoxy; $C_2$-$C_4$ alkenyl optionally substituted by phenyl; $C_3$-$C_6$ cycloalkyl; phenyl optionally substituted by $C_1$-$C_8$ alkoxy; or heteroaryl selected from the group consisting of furyl, thienyl, isoxazolyl, and pyridyl optionally substituted by halogen or $C_1$-$C_8$ alkyl; and (vi) —$PO(OR_{11})_2$, —$CH_2$—O—$PO(OR_{11})_2$ or —$CH(CH_3)$—O—$PO(OR_{11})_2$, wherein $R_{11}$ is independently selected from the group consisting of H, $C_1$-$C_8$ alkyl, and $C_1$-$C_8$ alkyl optionally substituted by hydroxy, $C_1$-$C_8$ alkoxy, or $C_1$-$C_8$ (alkyl)carbonyloxy;

$R_2$ and $R_3$ each independently is H, $C_1$-$C_8$ alkyl, Cl or F, or halo($C_1$-$C_8$)alkyl;

$R_4$ is H or $C_1$-$C_8$ alkyl, and $R_5$ is propargyl, allyl, or cyclobutyl;

$R_6$ is H, $C_1$-$C_8$ alkyl, $C_1$-$C_8$ alkoxy, mercapto, $C_1$-$C_8$ alkylthio, hydroxy, mercapto, amino, $C_1$-$C_8$ alkylamino, di($C_1$-$C_8$)alkylamino or oxo, thioxo, imino, or $C_1$-$C_8$ alkylimino at the 2- or 4-position of the ring;

$R_7$ is H, halogen, $C_1$-$C_8$ alkyl, perhalo $C_1$-$C_8$ alkyl, $C_3$-$C_8$ cycloalkyl, $C_1$-$C_8$ alkoxy, $C_1$-$C_8$ alkylthio, hydroxy, mercapto, amino, $C_1$-$C_8$ alkylamino, di($C_1$-$C_8$)alkylamino, cyano, $C_1$-$C_8$ alkylsulfonyl, $C_1$-$C_8$ alkylcarbonylamino, $C_1$-$C_8$alkylcarbonyl($C_1$-$C_8$)amino, or $C_1$-$C_8$alkylsulfonyl($C_1$-$C_8$)amino;

each of the dotted lines indicates a single or double bond; and n is 0-8, and pharmaceutically acceptable salts thereof, but excluding the compounds wherein $R_1$, $R_2$, $R_3$, $R_6$, $R_7$ are H; n is 0; $R_4$ is H or $CH_3$, and $R_5$ is propargyl, or $R_1$, $R_2$, $R_3$, $R_4$, $R_6$, $R_7$ are H; n is 1, and $R_5$ is propargyl.

2. The compound according to claim 1, of the formula Ia:

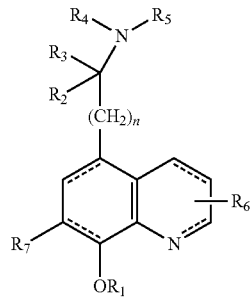

wherein $R_1$ to $R_7$ are as defined in claim 1.

3. The compound according to claim 2, of the formula II:

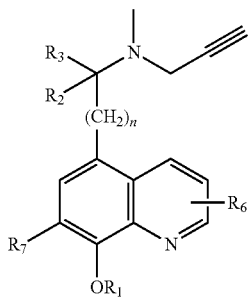

wherein
$R_1$, $R_2$, $R_3$ and $R_7$ are as defined in claim 1, $R_6$ is H and n is 0-2.

4. The compound according to claim 3, selected from the group consisting of (i) the compound wherein $R_1$, $R_2$, $R_3$ and $R_6$ each is H, n is 0, and $R_7$ is $CH_3$ or F, herein identified as compounds 1 and 2, respectively; (ii) the compound wherein $R_1$, $R_2$, $R_6$ and $R_7$ each is H, n is 0, and $R_3$ is $CH_3$ or $CF_3$; and
(iii) the compound wherein $R_1$, $R_6$ and $R_7$ each is H, and $R_2$ and $R_3$ each is F.

5. The compound according to claim 3, wherein $R_1$ is $C_1$-$C_3$ alkyl substituted by hydroxy, such as hydroxyethyl, hydroxypropyl; cyano, such as cyanomethyl; carboxy, such as carboxymethyl; or $C_1$-$C_3$ alkoxy, such as methoxypropyl, methoxyethyl or propoxymethyl.

6. The compound according to claim 3, wherein $R_1$ is —$COR_8$ and $R_8$ is $C_1$-$C_5$ alkyl such as methyl optionally substituted by methoxy, methoxycarbonyl, methylcarbonyloxy or one or more of Cl or F atoms, such as methoxymethyl, methoxycarbonylmethyl, methylcarbonyloxymethyl, chloromethyl or trifluoromethyl, ethyl optionally substituted by ethoxy, isobutyl, or sec-pentyl; $C_2$-$C_4$ alkenyl such as vinyl optionally substituted by phenyl, such as 2-phenylvinyl, 1-methylvinyl, 2-methylvinyl, 2,2-dimethylvinyl, or but-3-en-1-yl; $C_3$-$C_5$ cycloalkyl such as cyclopropyl or cyclopentyl; aryl such as phenyl optionally substituted by methoxy; heteroaryl such as 2-thienyl, 2-furyl, 5-isoxazolyl or pyridyl optionally substituted by Cl; or heterocyclyl such as 4-morpholinyl.

7. The compound according to claim 3, wherein $R_1$ is —$COR_8$ and $R_8$ is straight or branched $C_1$-$C_5$ alkyl substituted by amino at the α-position to the CO group, and the alkyl is optionally further substituted at a different position by hydroxy, amino, guanidino, mercapto, methylthio, carboxy, aminocarbonyl, phenyl, 4-hydroxyphenyl, 2-indolyl or 5-imidazolyl to form an amino acid residue derived from glycine, alanine, valine, leucine, isoleucine, serine, threonine, lysine, arginine, cysteine, methionine, aspartic, glutamic, asparagine, glutamine, phenylalanine, tyrosine, tryptophan or histidine.

8. The compound according to claim 3, wherein $R_1$ is —$COOR_9$ and $R_9$ is $C_1$-$C_8$ alkyl such as methyl optionally substituted by Cl, 4-nitrophenyl or $C_6$ cycloalkyl, ethyl optionally substituted by methoxy, such as 2-methoxyethyl, or one or more Cl or F atoms, such as 1-chloroethyl, 2-chloroethyl, 2-fluoroethyl, 2,2,2-trichloroethyl, or 2,2,2-trifluoroethyl, propyl, butyl, isobutyl, pentyl, or octyl; $C_2$-$C_3$ alkenyl such as vinyl, 1-methylvinyl or allyl; $C_3$-$C_4$ alkynyl such as propargyl or but-3-yn-yl; $C_5$-$C_6$ cycloalkyl such as cyclopentyl or cyclohexyl; or phenyl optionally substituted by nitro, fluoro, methoxy or methyl such as 4-nitrophenyl, 4-fluorophenyl, 4-methoxyphenyl, or 4-methylphenyl.

9. The compound according to claim 3, wherein $R_1$ is —$CH_2$—O—CO—$R_{10}$, or —$CH(CH_3)$—O—CO—$R_{10}$ and $R_{10}$ is $C_1$-$C_5$ alkyl such as methyl optionally substituted by methoxy, methoxycarbonyl, methylcarbonyloxy, or one or more Cl or F atoms, such as chloromethyl of trifluoromethyl, ethyl optionally substituted by ethoxy, isobutyl, or 1-methylbutyl; $C_2$-$C_4$ alkenyl such as vinyl optionally substituted by phenyl, such as 2-phenylvinyl, 1-methylvinyl, 2-methylvinyl, 3-buten-1-yl, or 2,2-dimethylvinyl; $C_3$-$C_5$ cycloalkyl such as cyclopropyl or cyclopentyl; phenyl optionally substituted by methoxy such as 4-methoxyphenyl; or heteroaryl such as 2-furyl, 2-thienyl, 5-isoxazolyl, or pyridyl optionally substituted by halogen such as 2-chloro-pyrid-5-yl.

10. The compound according to claim 1, wherein
(i) $R_1$, $R_2$, $R_3$, $R_6$ and $R_7$ each is H; $R_4$ is $CH_3$, $R_5$ is propargyl, and the two dotted lines in the heterocylic ring represent single bonds; or
$R_1$, $R_2$, $R_3$, $R_6$ and $R_7$ each is H; $R_4$ is $CH_3$, $R_5$ is propargyl, and the two dotted lines in the carbocyclic ring represent single bonds.

11. The compound according to claim 3 or a pharmaceutically acceptable salt thereof, wherein $R_1$, $R_2$, $R_3$, $R_6$, and $R_7$ each is H, and n is 1, herein identified as compound 3.

12. The compound according to claim 3 or a pharmaceutically acceptable salt thereof, wherein $R_1$, $R_2$, $R_3$, and $R_6$ each is H, $R_7$ is cyclopropyl, and n is 1, herein identified as compound 7.

13. The compound according to claim 3 or a pharmaceutically acceptable salt thereof, wherein $R_1$, $R_2$, $R_3$, and $R_6$ each is H, $R_7$ is F, and n is 1, herein identified as compound 8.

14. The compound according to claim 3 or a pharmaceutically acceptable salt thereof, wherein $R_1$, $R_2$, $R_3$, $R_6$, and $R_7$ each is H, and n is 2, herein identified as compound 4.

15. A pharmaceutical composition comprising a compound according to claim 1, or a pharmaceutically acceptable salt thereof, and a pharmaceutically acceptable carrier.

16. A cosmetic composition comprising a compound according to claim 1, and a cosmetically acceptable carrier.

17. A compound of the formula III:

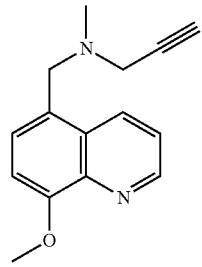

18. A pharmaceutical composition comprising a compound according to claim 17, or a pharmaceutically acceptable salt thereof, and a pharmaceutically acceptable carrier.

19. The compound of claim 11 in the form of a pharmaceutically acceptable salt selected from the group consisting of hydrochloride, citrate, and methanesulfonate.

* * * * *